(12) United States Patent
Ichikawa et al.

(10) Patent No.: US 9,125,663 B2
(45) Date of Patent: Sep. 8, 2015

(54) TREATMENT INSTRUMENT SYSTEM WITH THERMALLY DEFORMABLE ABSORBENT MEMBER AND SLIDABLE HOLDING SURFACE

(71) Applicant: OLYMPUS MEDICAL SYSTEMS CORP., Tokyo (JP)

(72) Inventors: Hiroaki Ichikawa, Yokohama (JP); Hideyuki Kasahara, Hamura (JP); Hiroshi Kakidachi, Hino (JP); Masato Tamai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 246 days.

(21) Appl. No.: 13/668,861

(22) Filed: Nov. 5, 2012

(65) Prior Publication Data
US 2013/0172887 A1    Jul. 4, 2013

Related U.S. Application Data

(60) Provisional application No. 61/557,069, filed on Nov. 8, 2011.

(51) Int. Cl.
*A61B 18/14* (2006.01)
*A61B 17/08* (2006.01)
*A61B 18/08* (2006.01)
*A61B 17/064* (2006.01)
(Continued)

(52) U.S. Cl.
CPC .......... *A61B 18/1445* (2013.01); *A61B 17/064* (2013.01); *A61B 17/0643* (2013.01); *A61B 17/07207* (2013.01); *A61B 17/08* (2013.01); *A61B 17/083* (2013.01); *A61B 18/085* (2013.01); *A61B 2018/0063* (2013.01)

(58) Field of Classification Search
CPC .......... A61B 18/1442; A61B 18/1445; A61B 18/08; A61B 18/082; A61B 18/085; A61B 18/12; A61B 2018/145; A61B 2018/00589; A61B 2018/00595; A61B 2018/0063; A61B 17/064; A61B 17/0644; A61B 17/068; A61B 17/0684; A61B 17/0686; A61B 17/072; A61B 17/07207; A61B 17/115
USPC ........ 606/41, 51, 52, 139, 142, 143, 219, 220
See application file for complete search history.

(56) References Cited

U.S. PATENT DOCUMENTS 5,551,622 A * 9/1996 Yoon .......................... 227/178.1
6,488,196 B1 12/2002 Fenton, Jr.
8,348,127 B2 * 1/2013 Marczyk .................... 227/177.1
(Continued)

*Primary Examiner* — Carl H Layno
*Assistant Examiner* — Eugene Wu
(74) *Attorney, Agent, or Firm* — Oliff PLC

(57) ABSTRACT

A treatment system includes: an absorbent member which is arranged to be discharged into the biological tissues as the fusion targets from the first jaw, thermally deformed when the thermal energy is applied thereto; a first energy discharge portion which is configured to discharge the absorbent member toward the second holding surface, and which is configured to supply the high-frequency energy and the thermal energy to the biological tissues; a second energy discharge portion which is configured to come into contact with at least a part of the absorbent member when the absorbent member is discharged, and which is configured to supply the high-frequency energy and the thermal energy to the biological tissues; and a control unit which is configured to control the energy source to supply the thermal energy after discharging the absorbent member to the biological tissues.

9 Claims, 15 Drawing Sheets

(51) Int. Cl.
*A61B 17/072* (2006.01)
*A61B 18/00* (2006.01)

(56) References Cited

U.S. PATENT DOCUMENTS

| | | | |
|---|---|---|---|
| 2004/0059378 A1* | 3/2004 | Peterson et al. | 606/219 |
| 2005/0072827 A1* | 4/2005 | Mollenauer | 227/180.1 |
| 2005/0184121 A1* | 8/2005 | Heinrich | 227/175.1 |
| 2006/0167452 A1 | 7/2006 | Moses et al. | |
| 2008/0287989 A1* | 11/2008 | Weisel et al. | 606/220 |
| 2009/0048589 A1* | 2/2009 | Takashino et al. | 606/28 |
| 2009/0081313 A1* | 3/2009 | Aghion et al. | 424/641 |
| 2009/0118748 A1 | 5/2009 | Pugsley et al. | |
| 2009/0272785 A1* | 11/2009 | Sonnenschein et al. | 227/176.1 |
| 2010/0230464 A1* | 9/2010 | Knodel et al. | 227/175.1 |
| 2011/0034926 A1* | 2/2011 | Menneking et al. | 606/62 |
| 2011/0248064 A1* | 10/2011 | Marczyk | 227/114 |

* cited by examiner

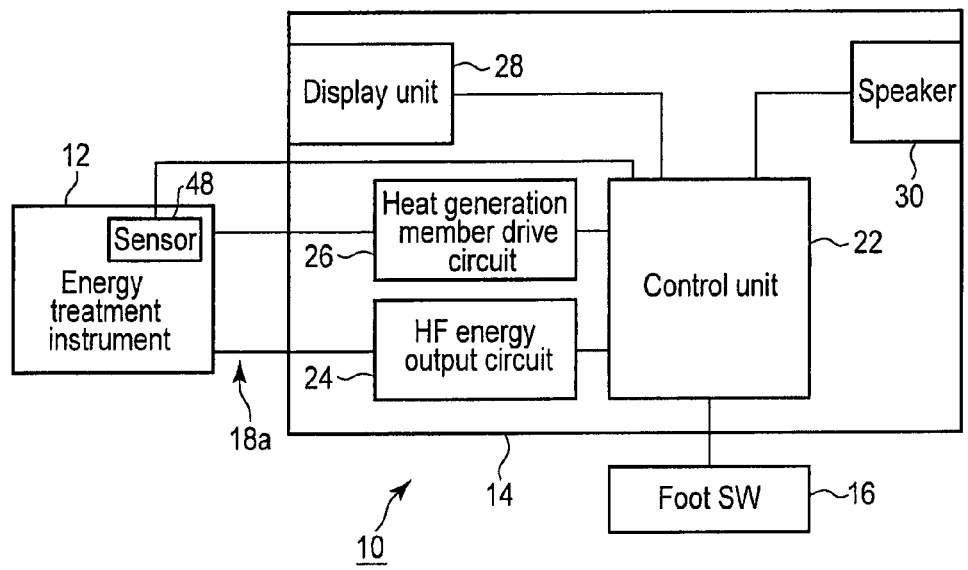
F I G. 2
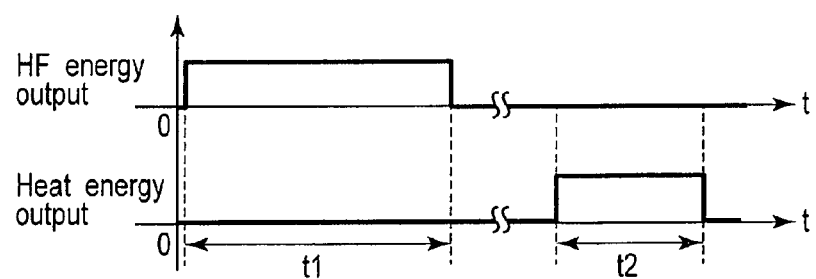
F I G. 3

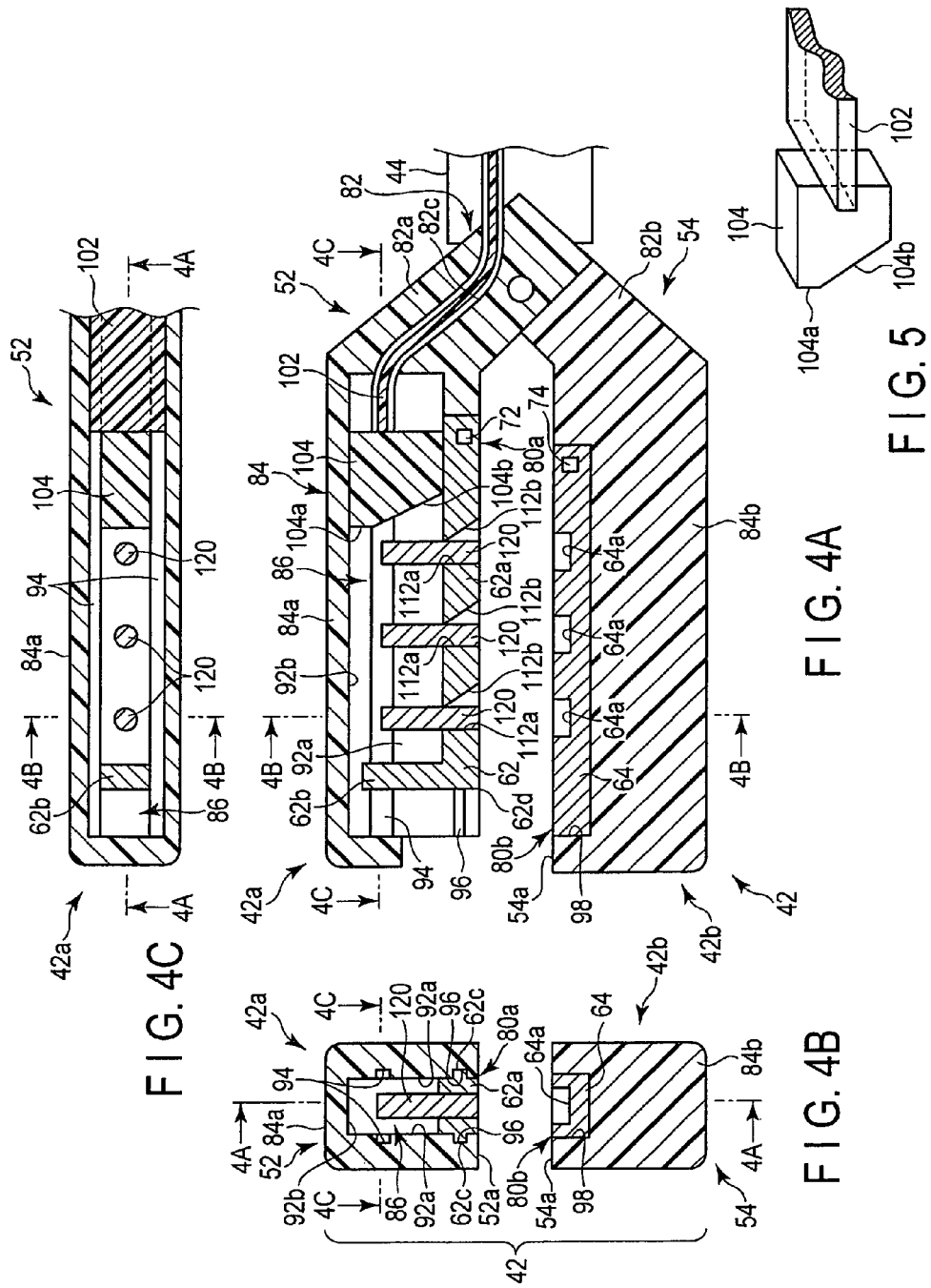

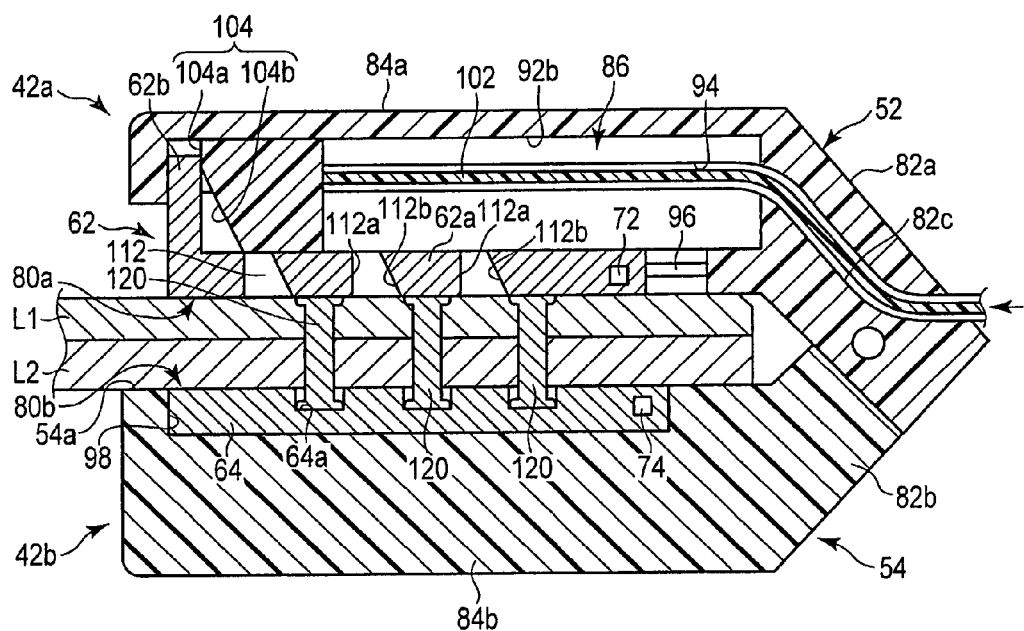
F I G. 6C

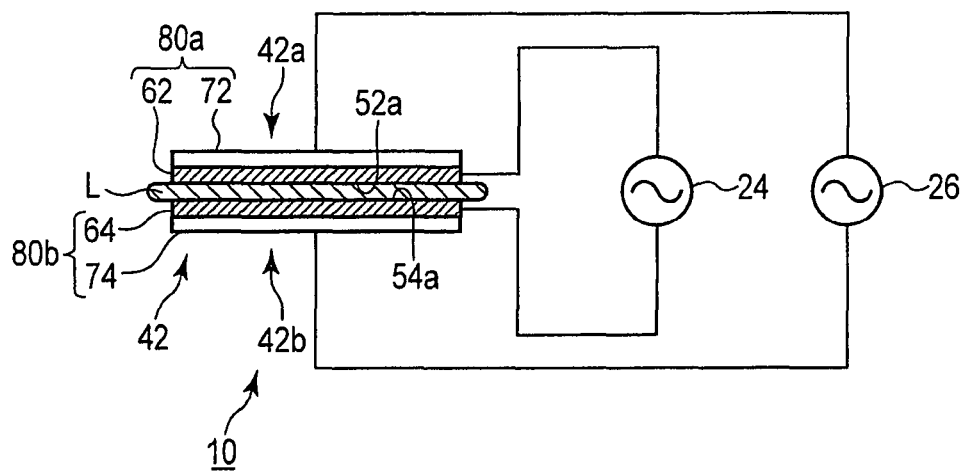
F I G. 7A
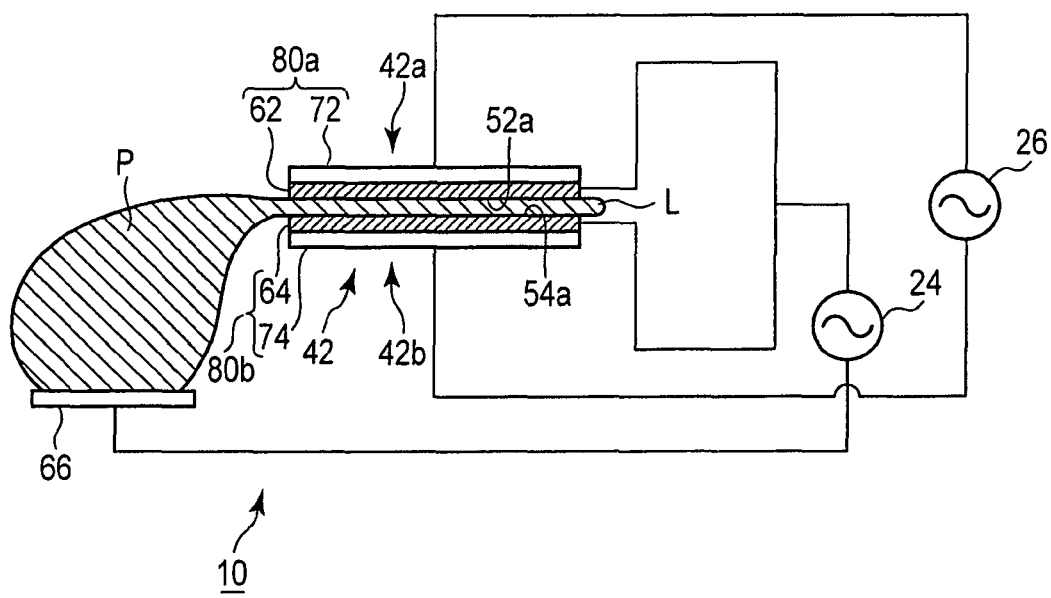
F I G. 7B

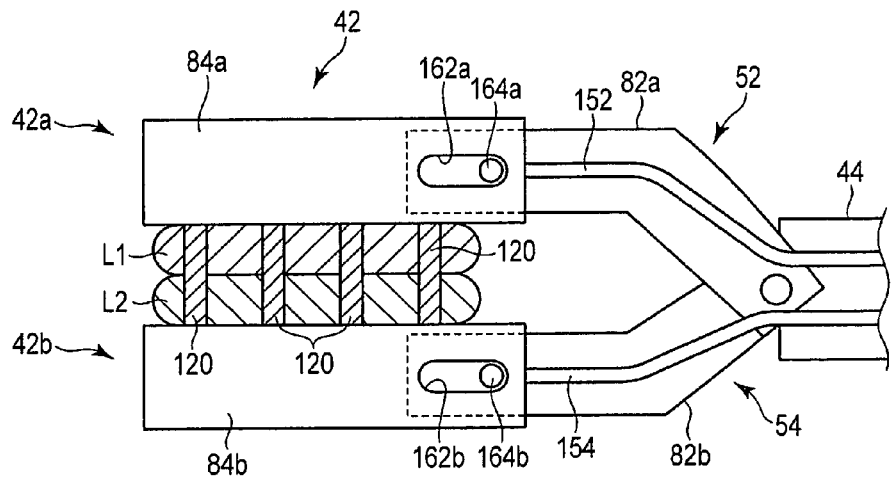
F I G. 9A
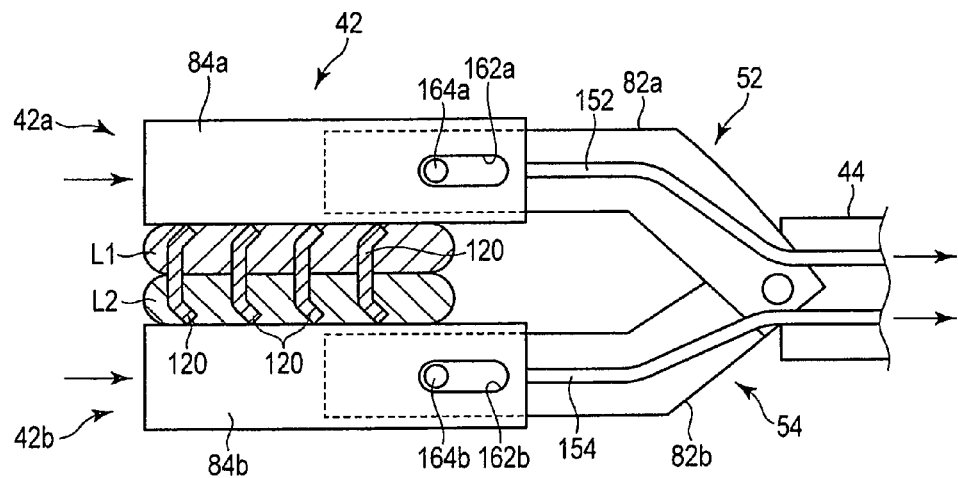
F I G. 9B

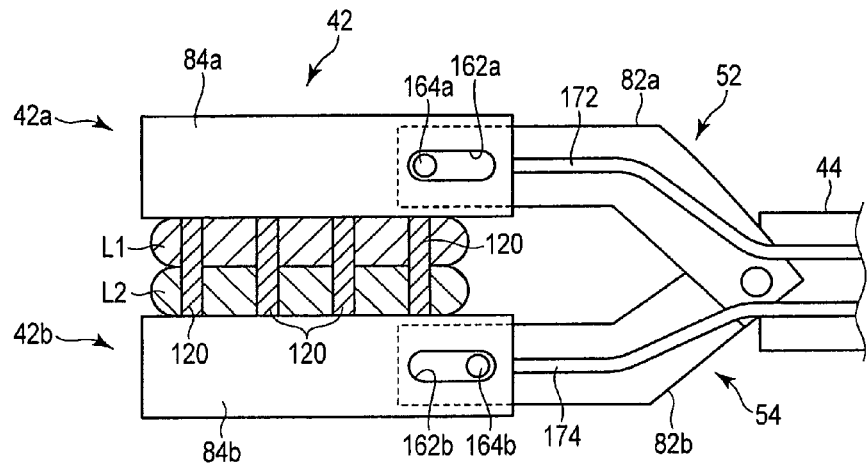
F I G. 10A
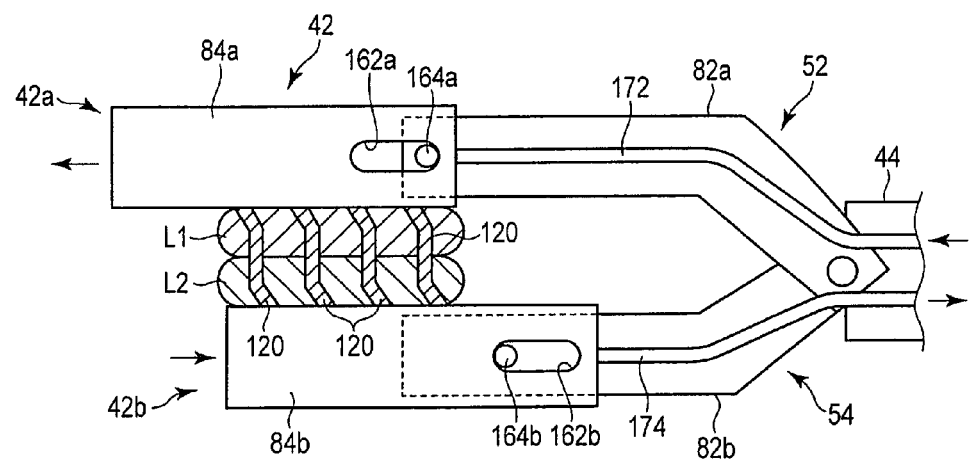
F I G. 10B

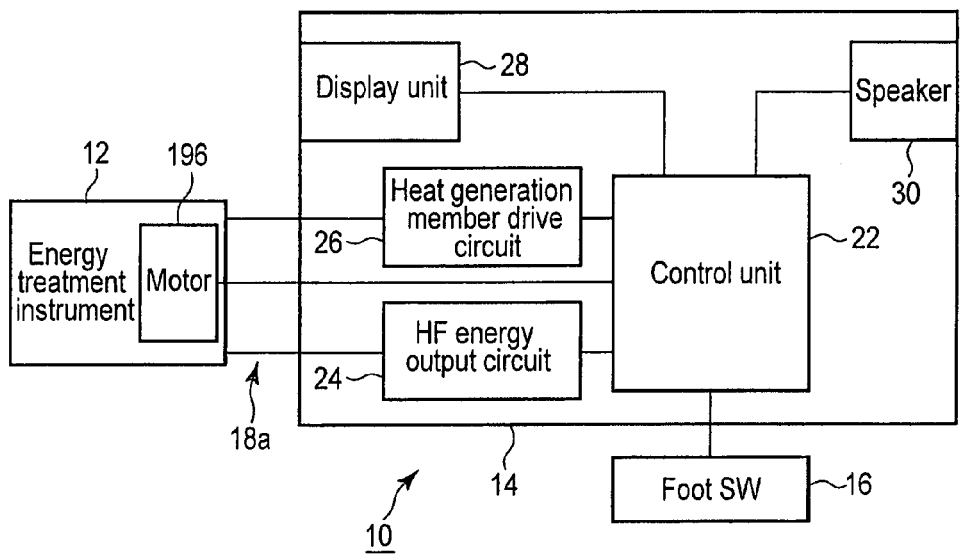
F I G. 12
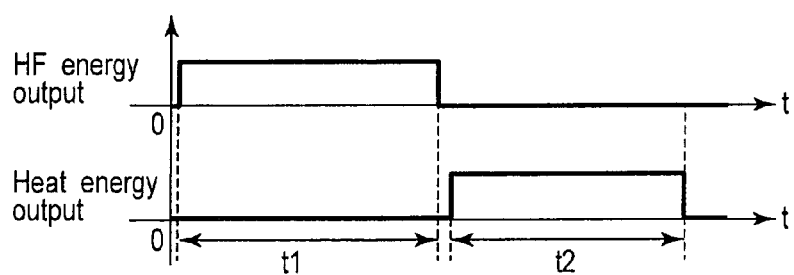
F I G. 13

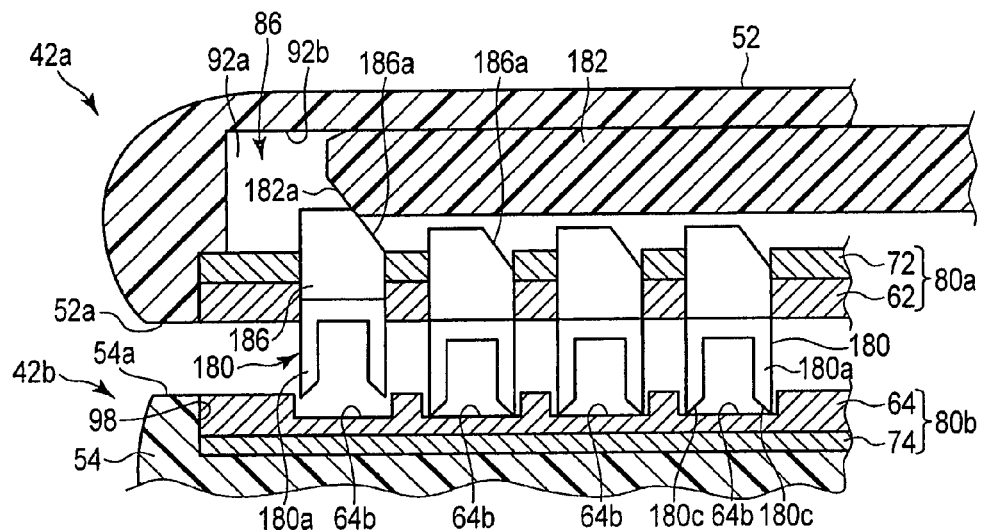
F I G. 14
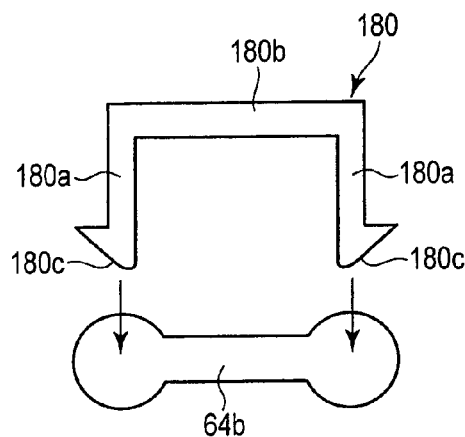
F I G. 15A
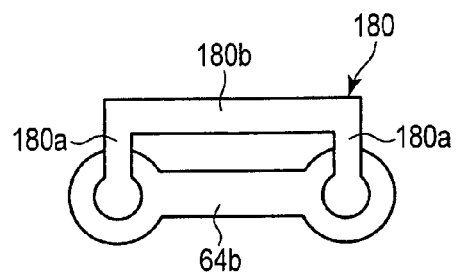
F I G. 15B

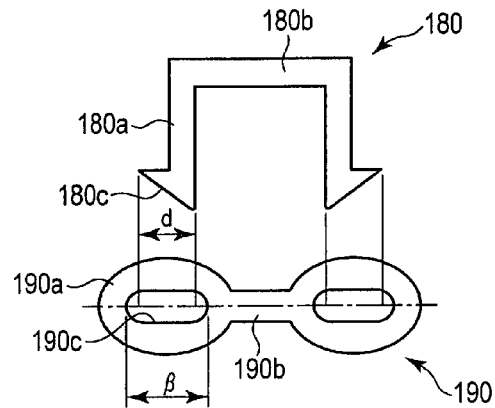
F I G. 16A
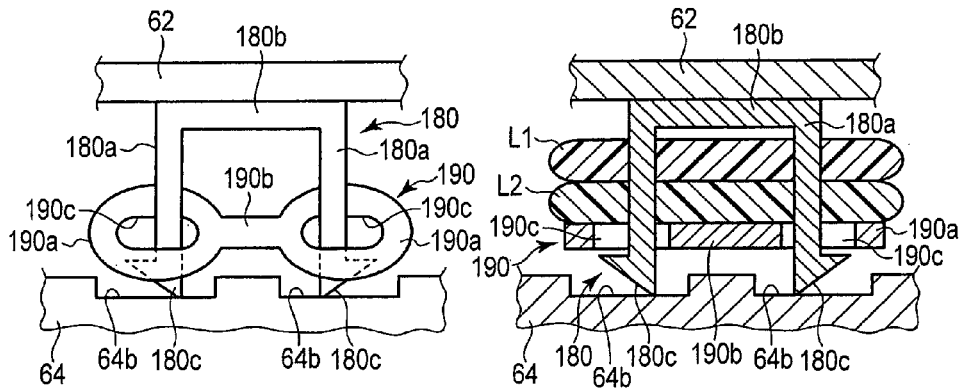
F I G. 16B        F I G. 16C
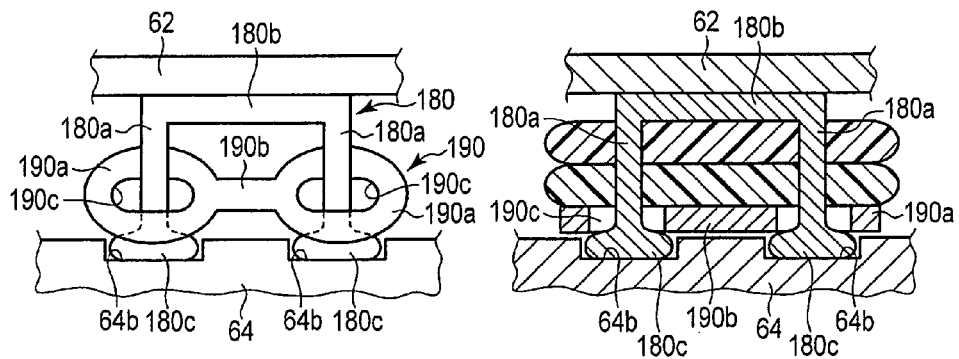
F I G. 16D        F I G. 16E

TREATMENT INSTRUMENT SYSTEM WITH THERMALLY DEFORMABLE ABSORBENT MEMBER AND SLIDABLE HOLDING SURFACE

CROSS-REFERENCE TO RELATED APPLICATIONS

This application is based upon and claims the benefit of priority from the prior U.S. Provisional Application No. 61/557,069, filed Nov. 8, 2011, the entire contents of which are incorporated herein by reference.

BACKGROUND OF THE INVENTION

1. Field of the Invention

The present invention relates to a treatment instrument system which is configured to apply energy to a biological tissue as a fusion target and treat the biological tissue.

2. Description of the Related Art

There are treatment instruments that use various kinds of energy in place of a stapler and give a treatment, to connect biological tissues. For example, as energy, high-frequency energy and thermal energy are combined, biological tissues are denatured, and then the biological tissues are dehydrated, whereby the biological tissue can be connect.

BRIEF SUMMARY OF THE INVENTION

In an aspect of the present invention, a treatment system configured to apply energy to biological tissues as fusion targets and give a treatment to the biological tissues, includes: an energy source which is configured to generate high-frequency energy and thermal energy; an insertion portion which includes a distal end portion, a proximal end portion, and a longitudinal direction defined by the distal end portion and the proximal end portion, and which is extended from the proximal end portion toward the distal end portion along the longitudinal direction; a first jaw which is provided at the distal end portion of the insertion portion and includes a first holding surface; a second jaw which is provided at the distal end portion of the insertion portion, and which includes a second holding surface that faces the first holding surface and that is configured to hold the biological tissues as the fusion targets in cooperation with the first holding surface; an absorbent member which is arranged to be discharged into the biological tissues as the fusion targets from the first jaw through the first holding surface, thermally deformed when the thermal energy is applied thereto, and configured to be absorbed into the biological tissues as the fusion targets with time while being arranged in the biological tissues as the fusion targets; a first energy discharge portion which is slidably provided on the first holding surface along the longitudinal direction, which is configured to discharge the absorbent member toward the second holding surface through the first holding member when it slides along the longitudinal direction, and which is configured to supply the high-frequency energy and the thermal energy to the biological tissues; a second energy discharge portion which is provided on the second holding surface, which is configured to come into contact with at least a part of the absorbent member when the absorbent member is discharged, and which is configured to supply the high-frequency energy and the thermal energy to the biological tissues; and a control unit which is configured to control the energy source to enable application of the high-frequency energy and the thermal energy to the biological tissues as the fusion targets in the mentioned order through at least one of the first energy discharge portion and the second energy discharge portion, and which is configured to control the energy source to supply the thermal energy after discharging the absorbent member to the biological tissues.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic view showing the energy treatment system according to the first embodiment;

FIG. 3 is a schematic view showing output states of energy from a high-frequency energy output circuit and a thermal energy output circuit in an energy sources in the energy treatment system according to the first embodiment;

FIG. 4A is a schematic longitudinal cross-sectional view taken along a line 4A-4A in each of FIG. 4B and FIG. 4C, showing a treatment portion of a treatment instrument in the energy treatment system according to the first embodiment;

FIG. 4B is a schematic longitudinal cross-sectional view taken along a line 4B-4B in each of FIG. 4A and FIG. 4B, showing the treatment portion of the treatment instrument in the energy treatment system according to the first embodiment;

FIG. 4C is a schematic transverse cross-sectional view taken along a line 4C-4C in each of FIGS. 4A and 4C, showing the treatment portion of the treatment instrument in the energy treatment system according to the first embodiment;

FIG. 5 is a schematic perspective view showing a pusher and a slider in the energy treatment system according to the first embodiment;

FIG. 6C is a schematic longitudinal cross-sectional view taken along a line 4A-4A in each of FIG. 4B and FIG. 4C, showing a state that the pins penetrate through the biological tissues and then both ends of each pin are heated while holding the biological tissues between the electrodes of the treatment portion of the treatment instrument in the energy treatment system according to the first embodiment;

FIG. 7A is a schematic view showing that the treatment instrument according to the first embodiment is of a bipolar type;

FIG. 7B is a schematic view showing that the treatment instrument according to the first embodiment is of a monopolar type;

FIG. 9A is a schematic view showing a treatment portion of a treatment instrument in an energy treatment system according to a second modification of the first embodiment;

FIG. 9B is a schematic view showing the treatment portion of the treatment instrument in the energy treatment system according to the second modification of the first embodiment;

FIG. 10A is a schematic view showing a treatment portion of a treatment instrument in an energy treatment system according to a third modification of the first embodiment;

FIG. 10B is a schematic view showing the treatment portion of the treatment instrument in the energy treatment system according to the third modification of the first embodiment;

FIG. 12 is a schematic view showing the energy treatment system according to the fourth modification of the first embodiment;

FIG. 13 is a schematic view showing output states of energy from a high-frequency energy output circuit and a thermal energy output circuit in an energy sources in an energy treatment system according to the fourth modification of the first embodiment;

FIG. 14 is a schematic longitudinal cross-sectional view taken along a line 11C-11C in FIG. 11A, showing a treatment portion of a treatment instrument in an energy treatment system according to a fifth modification of the first embodiment;

FIG. 15A is a schematic view showing a relationship between a staple driven from an electrode arranged in a first jaw and a receiving portion of an electrode arranged in a second jaw in the treatment portion of the treatment instrument in the energy treatment system according to the fifth modification of the first embodiment;

FIG. 15B is a schematic view showing a state that leg portions of the staple driven from the electrode arranged in the first jaw are allowed to come into contact with the receiving portion of the electrode arranged in the second jaw and thermal energy is applied to the staple from the electrodes in the treatment portion of the treatment instrument in the energy treatment system according to the fifth modification of the first embodiment;

FIG. 16A is a schematic view showing that a staple receiving portion arranged on an electrode placed in a second jaw is put to face a staple driven from an electrode arranged in a first jaw in a treatment portion of a treatment instrument in an energy treatment system according to a sixth modification of the first embodiment;

FIG. 16B is a schematic view showing a state that leg portions of the staple are arranged to come into contact with a receiving portion on the electrode arranged in the second jaw while the leg portions of the staple driven from the electrode arranged in the first jaw are inserted in the staple receiving portion in the treatment portion of the treatment instrument in the energy treatment system according to the sixth modification of the first embodiment;

FIG. 16C is a schematic cross-sectional view showing that the leg portions of the staple are arranged to come in contact with the receiving portion of the electrode arranged in the second jaw while the leg portions of the staple driven from the electrode arranged in the first jaw are inserted in the staple receiving portion in the treatment portion of the treatment instrument in the energy treatment system according to the sixth modification of the first embodiment;

FIG. 16D is a schematic view showing a state that the leg portions of the staple driven from the electrode arranged in the first jaw are arranged to come into contact with the receiving portion of the electrode arranged in the second jaw, thermal energy is applied to the leg portions of the staple from the electrodes, and the leg portions of the staple are deformed in the treatment portion of the treatment instrument in the energy treatment system according to the sixth modification of the first embodiment;

FIG. 16E is a schematic cross-sectional view showing a state that the leg portions of the staple driven from the electrode arranged in the first jaw are arranged to abut on the receiving portion of the electrode arranged in the second jaw, thermal energy is applied to the leg portions of the staple from the electrodes, and the leg portions of the staple are deformed in the treatment portion of the treatment instrument in the energy treatment system according to the sixth modification of the first embodiment;

DETAILED DESCRIPTION OF THE INVENTION

A mode for carrying out the present invention will now be described hereinafter with reference to the drawings.

A first embodiment will be explained with reference to FIG. 1 to FIG. 7B.

Figure 1:
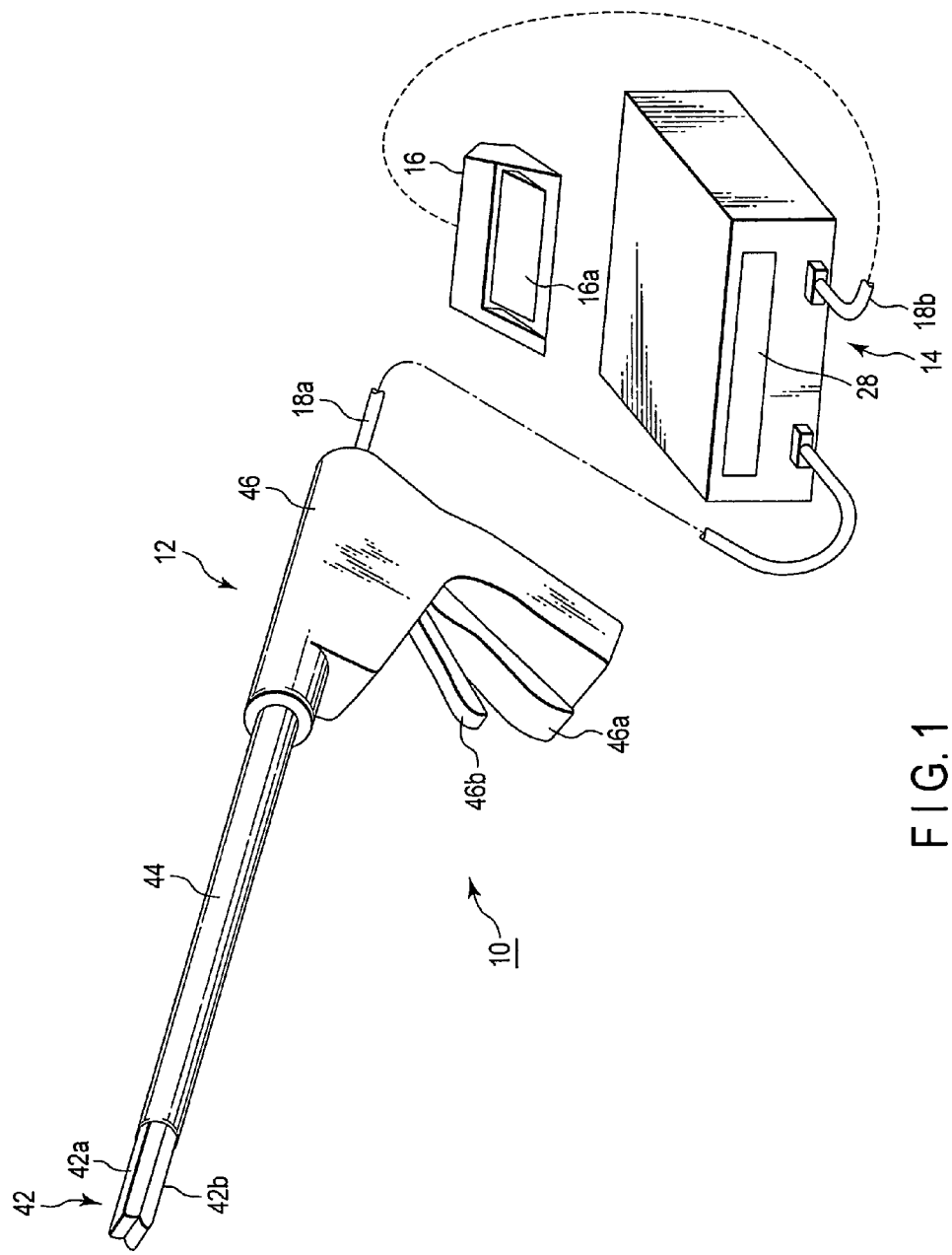
FIG. 1 is a schematic view showing an energy treatment system according to a first embodiment.

As shown in FIG. 1, a treatment system 10 using energy according to this embodiment includes a treatment instrument (an energy treatment instrument) 12 and an energy source 14 which generates energy that is supplied to the treatment instrument 12. The energy source 14 is connected to a foot switch 16 having a pedal 16a configured to switch ON/OFF of the energy that is given to the treatment instrument 12. The treatment instrument 12 is electrically connected to the energy source 14 through a first cable 18a obtained by bundling lead wires or signal lines, and the energy source 14 is electrically connected to the foot switch 16 through a second cable 18b obtained by bundling lead wires or signal lines. The foot switch 16 can input a signal to the energy source 14 by, e.g., an operation of the pedal 16a, and the energy source 14 can control energy that is supplied to the treatment instrument 12 based on, e.g., an operation of the pedal 16a of the foot switch 16.

As shown in FIG. 2, the energy source 14 includes a control unit 22, a high-frequency energy output circuit 24, a heat generation member drive circuit 16, a display unit 28, and a speaker 30. That is, the energy source 14 can generate high-frequency energy and thermal energy and supply them to the treatment instrument 12.

Here, the high-frequency energy output circuit 24 in the energy source 14 is controlled by the control unit 22, supplies the high-frequency energy to later-described electrodes 62 and 64 of the treatment instrument 12, and heats biological tissues L1 and L2 held between the electrodes 62 and 64. Further, the biological tissue L1 and L2 are denatured by the thermal energy. The heat generation member drive circuit 26 in the energy source 14 is controlled by the control unit 22, supplies energy to heat generation members (resistive heaters) 72 and 74, and enables the heat generation members 72 and 74 to generate heat. Furthermore, the heat (thermal energy) is transferred from the heat generation members 72 and 74 to the high-frequency electrodes 62 and 64, the heat (the thermal energy) is transferred to the biological tissues L1 and L2, and the biological tissue L1 and L2 are dehydrated. The display unit 28 is controlled by the control unit 22. As the display unit 28, it is preferable to use, e.g., a touch panel so that this touch panel can be used in case of displaying states of the energy source 14 or configuring various kinds of settings. Further, the speaker 30 is controlled by the control unit 22 so that sound can be used for informing of ON/OFF of an output from the high-frequency energy output circuit 24 or the heat generation member drive circuit 26.

It is to be noted that, in this embodiment, the description is given as to the example where the energy source 14 includes the control unit 22, but the control unit 22 can be preferably arranged outside the energy source 14.

The control unit 22 in the energy source 14 can control, e.g., a supply time at a time of supplying the high-frequency energy (the thermal energy) using the later-described electrodes 62 and 64 of the treatment instrument 12 and the thermal energy using the later-described heat generation members 72 and 74 to the biological tissues L1 and L2. The control unit 22 controls the high-frequency energy output circuit 24 to output appropriate high-frequency energy for a time t1 as shown in FIG. 3 by pressing down the pedal 16a of the foot switch 16, stops the output, then controls the display unit 28 to inform an operator about end of a treatment using the later-described electrodes 62 and 64, and controls the speaker 30 to generate sound so that the operator can be aware of the end of the treatment using the later-described electrodes 62 and 64. Further, after treatment using the high-frequency energy, by presses down the pedal 16a of the foot switch 16, with later-described pins 120 being stuck in the biological tissues L1 and L2, the control unit 22 controls the heat generation member drive circuit 26 to output appropriate thermal energy for a time t2, stops the output, then controls the display unit 28 to inform the operator about end of the treatment using the later-described heat generation members 72 and 74, and controls the speaker 30 to generate sound so that the operator can be aware of the end of the treatment using the later-described heat generation members 72 and 74.

It is to be noted that the control portion 22 may change the setting which outputs the appropriate high-frequency energy from the high-frequency energy output circuit 24 for the time t1, based on the setting in the display unit 28, to the setting which outputs the high-frequency energy using a change in biological information (e.g., an impedance or a phase difference) of the biological tissues L1 and L2 that can be measured by the electrodes 62 and 64, or it may stop output of the high-frequency energy when one of both the items (the time and the biological information) is attained faster than the other.

As shown in FIG. 1, the treatment instrument 12 includes a treatment portion 42 which gives a treatment to the biological tissues L1 and L2, an insertion portion 44, and an operation portion 46. The insertion portion 44 is extended from a proximal end portion at which the operation portion 46 is arranged toward a distal end portion at which the treatment portion 42 is arranged, and it is inserted into a hole together with the treatment portion 42.

As shown in FIG. 4A to FIG. 4C, the treatment portion 42 includes a pair of openable and closable jaws (first and second jaws) 52 and 54, high-frequency electrodes 62 and 64 arranged in the jaws 52 and 54, and heat generation members 72 and 74 arranged in the high-frequency electrodes 62 and 64. In these members, the high-frequency electrode 62 and the heat generation member 72 form a first energy discharge portion 80a to supply high-frequency and thermal energy, respectively, and the high-frequency electrode 64 and the heat generation member 74 form a second energy discharge portion 80b to supply high-frequency and thermal energy, respectively. Further, the first jaw 52, the high-frequency electrode 62 and the heat generation member 72 form a first holding portion 42a, and the second jaw 54, the high-frequency electrode 64 and the heat generation member 74 form a second holding portion 42b.

Opening/closing operations of the first and second jaws 52 and 54, i.e., opening/closing operations of the first and second holding portions 42a and 42b are operated by an opening/closing lever 46a of the operation portion 46. When the opening/closing lever 46a is operated, the first and second jaws 52 and 54 are opened/closed by well-known means such as a wire or a rod arranged in the insertion portion 44. It is to be noted that only one (see a second embodiment) or both of the first and second jaws 52 and 54 may be configured to be operated. That is, the first and second jaws 52 and 54 can be relatively opened/closed.

The first jaw 52 includes a holding surface 52a which is configured to face the second jaw 54 and hold a biological tissue. The second jaw 54 includes a second holding surface 54a which is configured to face the holding surface 52a of the first jaw 52 and holds a biological tissue in cooperation with the holding surface 52a of the first jaw 52. It is to be noted that, in case of actually holding a biological tissue, it is held between a set of the holding surface 52a of the first jaw 52a and a surface (a holding surface) of a tabular portion 62a of the electrode 62 and a set of the holding surface 54a of the second jaw 54 and a surface (a holding surface) of the electrode 64.

The high-frequency electrode 62 and 64 and the heat generation members 72 and 74 which are arranged to transfer heat to the high-frequency electrodes 62 and 64 are provided in the first and second jaws 52 and 54, respectively. As the heat generation members 72 and 74, heater elements may be used, or plate-like heaters may be used. If the heat generation members 72 and 74 are the heater elements, it is preferable for these members to be arranged or buried in back surfaces or side surfaces of the electrodes 62 and 64. If the heat generation members 72 and 74 are plate-like heaters, it is preferable for these members to be arranged on the back surfaces of the electrodes 62 and 64. It is also preferable for each of the heat generation members 72 and 74 to have a bar shape which is long in the longitudinal direction of the electrodes 62 and 64 or a direction orthogonal to the longitudinal direction. It is to be noted that, in this embodiment, a description will be given on the assumption that the heat generation members 72 and 74 as the heater elements are arranged on side surfaces of the electrodes 62 and 64.

The first and second jaws 52 and 54 are made of a material which has heat resisting properties and electrical insulating properties. Moreover, the high-frequency electrodes 62 and 64 face each other and used as part of the holding surfaces for the biological tissues L1 and L2. Therefore, when the high-frequency energy is supplied to the electrodes 62 and 64 while holding the biological tissues L1 and L2 between the electrodes 62 and 64, the biological tissues L1 and L2 may be heated and denatured. Additionally, the electrodes 62 and 64 are made of a material having excellent heat transfer properties. Therefore, when the heat generation members 72 and 74 are allowed to generate heat, this heat (thermal energy) is transferred to the electrodes 62 and 64, and this heat (the thermal energy) can be further transferred to the biological tissues L1 and L2 held between the electrodes 62 and 64.

As shown in FIG. 4A to FIG. 4C, the first jaw (an upper jaw) 52 includes a base portion 82 at which the second jaw (a lower jaw) 54 is supported to allow its opening and closing motions, and an extended portion 84 which is extended from the base portion 82 to the opposite side of the insertion portion 44 or the operation portion 46 and has a transverse cross section formed into a substantially U-like shape.

As shown in FIG. 4B, two pairs of concave groove portions 94 and 96 are formed on opposed inner peripheral surfaces 92a of the extended portion 84 of the first jaw 52, respectively. That is, in this embodiment, the two pairs of groove portions 94 and 96 are formed as concave portions. For example, a pusher 102 as a rectangular plate-like drive member is slidably arranged in each of one pair of groove portions 94 in the two pairs of groove portions 94 and 96. The electrode 62 is slidably arranged in each of the other pair of groove portions 96 in the two pairs of groove portions 94 and 96.

The electrode 62 includes a tabular portion 62a formed into a tabular shape that can slide along the opposed groove portions 96 and a stand-up portion 62b whose longitudinal cross section at a distal end thereof is formed into a substantially L-like shape. Here, the tabular portion 62a is engaged with each groove portion 96, but the stand-up portion 62b is not engaged with each groove portion 96. It is to be noted that an edge portion itself of the tabular portion 62a of the electrode 62 can be slidably engaged with each concave groove portion 96, or a convex portion 62c (see FIG. 4B) which is slidably engaged with each concave groove portion 96 may be continuously or discretely formed at the edge portion of the tabular portion 62a of the electrode 62.

The pusher 102 slidably arranged in each of the pair of groove portions 94 can be moved from the proximal end side toward the distal end side of the first jaw 52. The pusher 102 is formed into a tabular shape having appropriately flexibility, appropriately hardness, and electrical insulating properties like a rubber material. A guide path 82c through which the pusher 102 is slidably guided is formed in the base portion 82 of the first jaw 52. The guide path 82c is formed to be slightly larger than a board thickness and also slightly larger than a board width of the pusher 102. Therefore, the tabular pusher 102 is prevented from buckling when force is applied in the board thickness direction, and it can exercise pressing force in its axial direction.

A distal end of a non-illustrated rod is connected to a proximal end of the pusher 102, and a proximal end of the rod is connected to a slide lever 46b of the operation portion 46. Therefore, when the slide lever 46b of the operation portion 46 is moved toward the distal end side along the axial direction of the insertion portion 44, the distal end of the pusher 102 can be moved from the proximal end side toward the distal end side of the first jaw 52 through the non-illustrated rod. It is to be noted that, e.g., a moving amount detection sensor 48 that can detect movement of the pusher 102 with respect to the insertion portion 44 is arranged on the slide lever 46b, the pusher 102, or the non-illustrated rod, and the moving amount detection sensor 48 is connected to the control unit 22. Therefore, the control unit 22 can detect that the slide lever 46b has been operated and the pusher 102 has been moved by using the moving length detection sensor 48. That is, the control unit 22 can detect that later-described pins (absorbent members) 120 are discharged toward a biological tissue through the pusher 102 and a later-described slider 104.

The slider 104 having electrical insulating properties is fixed or integrally molded with respect to the distal end of the pusher 102. The slider 104 has an abutting surface 104a and an inclined surface 104b on a distal end surface thereof, and it is arranged to be slidable between a bottom surface 92b of the substantially U-shaped extended portion 84 of the first jaw 52 and the back surface of the tabular portion 62a of the electrode 62. It is preferable for a normal line of the abutting surface 104a of the slider 104 to be parallel to the axial direction of the insertion portion 44 or the extending direction (the longitudinal direction) of the extended portion 84a of the first jaw 52, and a normal line of the inclined surface 104b is inclined with respect to the axial direction of the insertion portion 44 or the extending direction (the longitudinal direction) of the extended portion 84a of the first jaw 52 and directed to the back surface of the tabular portion 62a of the electrode 62.

When the pusher 102 is moved forward along the groove portion 94, the contact surface 104a of the slider 104 is allowed to come into contact with the stand-up portion 62b at the distal end of the electrode 62. When the pusher 102 is further moved forward along the groove portion 94, since the stand-up portion 62b of the electrode 62 is pressed toward the distal end of the first jaw 52 by the abutting surface 104a of the slider 104, the electrode 62 can be moved toward the distal end of the first jaw 52.

It is to be noted that, as a longitudinal cross section of a boundary portion between the tabular portion 62a and the stand-up portion 62b at the distal end of the electrode 62, forming a curved surface (not shown) is preferable instead of forming a corner portion (an edge portion) 62d shown in FIG.

4A. That is, the distal end of the electrode 62 preferably has a shape with which the abutting surface 104*a* of the slider 104 is able to be in contact.

Openings 112, each of which is formed into an oval shape that is long in the longitudinal direction of the first jaw 52 on the surface side (the side facing the electrode 64 arranged in the second jaw 54) and into a circular shape on the back surface side (the side facing the bottom surface 92*b* of the extended portion 84), are formed in the tabular portion 62*a* of the electrode 62 at appropriate intervals. A circumferential length of each opening 112 in the board thickness direction of the tabular portion 62*a* of the electrode 62 is formed to be gradually shortened from the surface side toward the back surface side of the tabular portion 62*a*. Each opening 112 on the distal end side of the first jaw 52 is formed into a surface (an orthogonal surface) 112*a* orthogonal to the axial direction, and the same on the proximal end side is formed into an inclined surface 112*b*. A normal line of the inclined surface 112*b* is directed toward the electrode 64 of the second jaw 54.

In each opening 112 is arranged a pin (an absorbent member) 120 which is made of, e.g., a magnesium alloy material preferably having conductive properties, has biocompatible properties and bioabsorbable properties, and can be deformed when heat equal to or above a predetermined temperature is applied thereto. It is preferable for the pin 120 to have a circular transverse cross-sectional shape with a diameter of, e.g., 1 mm, and the pin 120 is preferably attached when press-fitted from the surface side of the tabular portion 62*a* of the electrode 62 toward the inside of the first jaw 52. At this time, it is preferable to press in the pin 120 until a lower end of the pin 120 (an end portion on the side close to the second jaw 54) is fitted to the surface of the tabular portion 62*a* of the electrode 62.

That is, a magazine 86 in which the electrode 62, the pusher 102, the slider 104, and the pins 120 are arranged is formed in the first jaw 52.

A tolerance relationship between the opening (a hole) 112 and the pin (a shaft) 120 is either loose fit or transition fit. In JISB-0401, for example, 1H6 is preferably designated as the opening (the hole), and 1h6 is preferably designated as the pin (the shaft) 120. Further, it is preferable to provide an accuracy of +0.006 mm as an upper limit for the diameter 1 mm of the opening (the hole) 112 and approximately 0 mm as a lower limit for the same, and an accuracy of 0 mm as an upper limit for the diameter 1 mm of the pin (the shaft) 120 and approximately −0.006 mm as a lower limit for the same. Therefore, although the pin 120 can be held on the back surface side in the opening 112, the pin 120 can be protruded from the surface side of the opening 112 while holding the pin 120 on the back surface side when the pin 120 is pressed with the slider 104. That is, in the relationship between the opening 112 and the pin 120, the pin 120 does not freely fall from the opening 112, but the pin 120 is formed to protrude from the surface of the tabular portion 62*a* of the electrode when pressed by the slider 104.

It is to be noted that the pin 120 made of magnesium or a magnesium alloy used in this embodiment has a crystal structure that hardly causes metal slip at an ordinary temperature (a hexagonal closest packing structure). Therefore, it is a metal material that is hardly bent or stretched at an ordinary temperature. It is known that, for example, when a temperature of magnesium is increased to approximately 200° C., the slip can be caused. Therefore, when each pin 120 is heated to, e.g., approximately 200° C., plastic deformation like bending or squashing the pin 120 can be caused.

It is to be noted that the pin (the absorbent member) 120 used in this embodiment is not restricted to magnesium or a magnesium alloy but a material having conductive properties is preferable and, for example, a material that is easily deformed (molten) at approximately 200° C. (thermal deformation) and absorbed into a biological tissue is desirable.

Figure 6A:
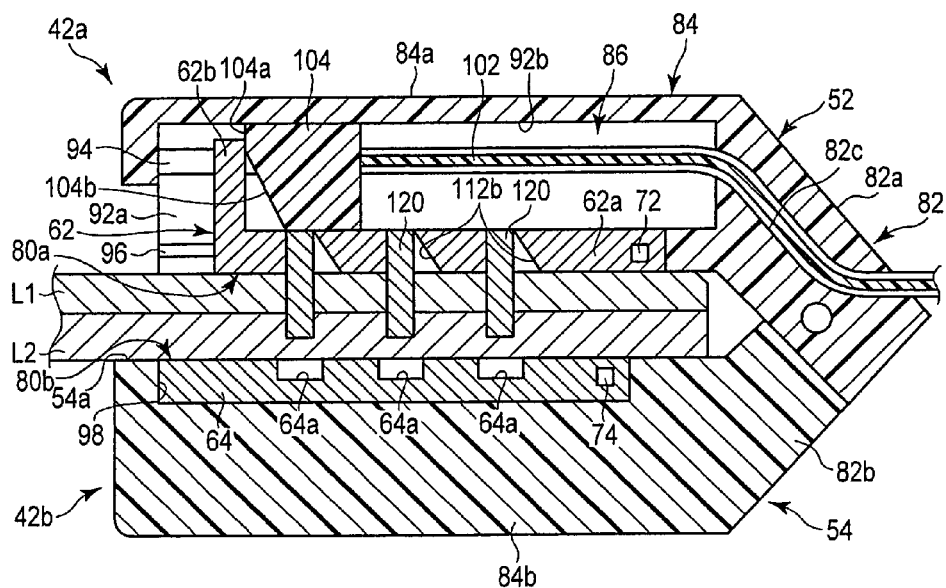
FIG. 6A is a schematic longitudinal cross-sectional view taken along a line 4A-4A in each of FIG. 4B and FIG. 4C, showing a state that pins are stuck into biological tissues while holding the biological tissues between electrodes of the treatment portion of the treatment instrument in the energy treatment system according to the first embodiment.

As shown in FIG. 4A and FIG. 4B, the second jaw (the lower jaw) 54 has a base portion 82*b* at which the first jaw (the upper jaw) 52 is supported to allow its opening and closing motions and an extended portion 84*b* which is extended from the base portion 82*b* to the opposite side of the insertion portion 44 or the operation portion 46. In the second jaw 54, a tabular electrode 64 having concave portions 64*a* is embedded in a recess 98. As shown in FIG. 4A and FIG. 6A, each concave portion 64*a* is placed at a position facing each opening 112 when the electrode 62 of the first jaw 52 is placed on the proximal end side. A heater element as the heat generation member 74 is attached to the electrode 64. The electrode 64 and the heat generation member 74 are connected to the energy source 14, respectively.

In a state shown in FIG. 4B, although the extended portion 84*b* of the second jaw 54 is shown as a solid member, forming the extended portion 84*b* as a hollow member (e.g., a transverse cross section has a substantially U-like shape) like the first jaw 52 is also preferable.

A brief description will now be given as to an operation of the treatment instrument system 10 according to this embodiment configured to apply energy to the biological tissues L1 and L2 as fusion targets and give a treatment to the biological tissues.

For example, the treatment portion 42 is set to face the biological tissues L1 and L2 to be connected. In this state, the opening/closing lever 46*a* of the operation portion 46 is operated, and the biological tissues L1 and L2 are held between the electrodes 62 and 64.

When a state that the pedal 16*a* of the foot switch 16 is being pressed using a foot is maintained, the control unit 22 of the energy source 14 supplies energy to the high-frequency electrodes 62 and 64 from the high-frequency energy output circuit 24. Therefore, the biological tissues L1 and L2 between the electrodes 62 and 64 are heated by using thermal energy (Joule heat) generated from the high-frequency energy. Further, the biological tissues L1 and L2 are denatured by the thermal energy, and then the supply of the energy to the high-frequency electrodes 62 and 64 is stopped. It is to be noted that the control unit 22 of the energy source 14 stops the output of the energy from the high-frequency energy output circuit 24 at earlier timing which is either timing when the biological tissues L1 and L2 between the high-frequency electrodes 62 and 64 reach a predetermined impedance value or a timing after the energy is given for the predetermined time t1.

Furthermore, the control unit 22 uses the high-frequency energy output circuit 24 and enables a non-illustrated weak reference current to the electrodes 62 and 64 to flow. The reference current is sufficiently smaller than energy required for generating heat in the biological tissues L1 and L2 between the electrodes 62 and 64 (see FIG. 3).

Here, when the predetermined impedance value has been reached or when the predetermined time t1 has passed, the energy source 14 stops the supply of the energy to the high-frequency electrodes 62 and 64 even though the pedal 16*a* of the foot switch 16 is being pressed down. On the other hand, when the foot is released from the pedal 16*a* before the predetermined impedance value is reached or before the predetermined time t1 passes, the energy source 14 stops the supply of the energy to the high-frequency electrodes 62 and 64 from the moment the foot is released. At this time, an interface between the biological tissues L1 and L2 is in a welded state.

After the supply of the high-frequency energy to the electrodes 62 and 64 is stopped, the state that the biological tissues L1 and L2 are gripped between the electrodes 62 and 64 arranged in the pair of jaws 52 and 54 is maintained, the slide lever 46b of the operation portion 46 is operated, and the pusher 102 is moved from the proximal end side (a position shown in FIG. 4A) toward the distal end side (a position shown in FIG. 6A) of the first jaw 52. At this time, the slider 104 moves from the proximal end side toward the distal end side, the upper ends of the pins 120 are sequentially pressed from the proximal end side toward the distal end side of the first jaw 52 by using the inclined surface 104b of the slider 104 as shown in FIG. 6A. Therefore, the pins 120 are moved to the lower side in the axial direction (the second jaw 52 side) and discharged from the first jaw 52 through the first holding surface 52a, and the respective pins 120 are stuck into the biological tissues L1 and L2 connected using the high-frequency energy.

In this state, the slide lever 46b is further operated, and the abutting surface 104a of the slider 104 is allowed to come in contact with the stand-up portion 62b of the distal end of the electrode 62. At this time, the lower ends of the respective pins 120 do not reach the concave portion 64a of the electrode 64 arranged in the second jaw 54 as shown in FIG. 6A.

Figure 6B:
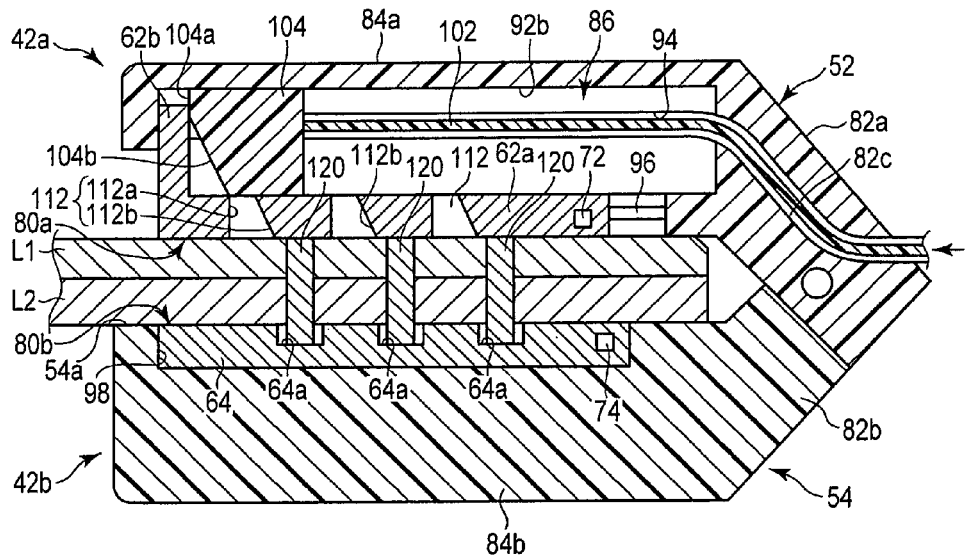
FIG. 6B is a schematic longitudinal cross-sectional view taken along a line 4A-4A in each of FIG. 4B and FIG. 4C, showing a state that the pins pierce through the biological tissues while holding the biological tissues between the electrodes of the treatment portion of the treatment instrument in the energy treatment system according to the first embodiment.

In the state that the abutting surface 104a of the slider 104 comes in contact with the erected portion 62b of the distal end of the electrode 62, the slide lever 46b is further operated, and the pusher 102 is further moved to the distal end side of the first jaw 52, whereby the electrode 62 moves from the proximal end side toward the distal end side of the first jaw 52 along the groove portion 96. At this time, the pins 120 are further pressed down and moved toward the lower side in the axial direction by the inclined surfaces 112b of the openings 112 in the tabular portion 62a of the electrode 62. Therefore, as shown in FIG. 6B, the lower ends of the pins 120 are arranged in the concave portions 64a formed in the surface of the electrode 64 arranged in the second jaw 54, and the upper ends of the pins 120 are arranged on the surface of the tabular portion 62a of the electrode 62 arranged in the first jaw 52. That is, the upper ends of the pins 120 are brought into contact with the surface of the tabular portion 62a of the electrode 62 arranged in the first jaw 52, and the lower ends of the pins 120 are brought into contact with the concave portions 64a of the electrode 64 arranged in the second jaw 54, respectively.

At this time, since the pins 120 have the conductive properties, the control unit 22 detects from the reference current that the high-frequency output circuit 24, the electrode 62 and 64, and the pins 120 have formed a closed circuit. When the control unit 22 detects the formation of such a closed circuit, the control unit 22 can output energy to the heat generation members 72 and 74 from the heat generation member drive circuit 26 in place of the already stopped output of energy from the high-frequency energy output circuit 24 to the electrodes 62 and 64. Furthermore, when the control unit 22 detects the formation of such a closed circuit, the control unit 22 controls the display unit 28, displays information that the energy can be output from the heat generation members 72 and 74 to the biological tissues, and generates sound from the speaker 30.

Furthermore, the moving amount detection sensor 48 detects a moving amount of the pusher 102, and the control unit 22 recognizes that the pins 120 have been discharged from the first jaw 52 and punctured into the biological tissues when the moving amount of the pusher 102 exceeds a predetermined moving amount. The control unit 22 can output the energy from the heat generation member drive circuit 26 to the heat generation members 72 and 74 in place of the already stopped output of the energy from the high-frequency energy output circuit 24 to the electrodes 62 and 64. Moreover, when the control unit 22 detects the formation of such a closed circuit, the control unit 22 controls the display unit 28, displays information that the energy can be output to the biological tissues from the heat generation members 72 and 74, and generates sound from the speaker 30. When the control unit 22 uses the moving amount detection sensor 48 and recognizes that the pins 120 have been discharged from the first jaw 52 and stuck into the biological tissues, the pins 120 do not have to have the conductive properties.

After the pins (the absorbent members) 120 have been discharged to the biological tissues in this manner, when the pedal 16a of the foot switch 16 is again pressed down, the energy is output from the heat generation member drive circuit 26, and the heat generation members 72 and 74 are allowed to generate heat. Therefore, the heat (the thermal energy) of the heat generation members 72 and 74 is transferred to the electrodes 62 and 64, and the biological tissues L1 and L2 can be dehydrated. Therefore, an amount of moisture in an interface of the biological tissues L1 and L2 can be reduced, and hence connection force of the biological tissues L1 and L2 can be increased.

Additionally, when the heat (the thermal energy) of the heat generation members 72 and 74 is transferred to the electrodes 62 and 64, and both ends of each of the pins 120 that are in contact with the electrodes 62 and 64 are heated, they are deformed (thermally deformed). At this time, as shown in FIG. 6C, diameters of both the ends of each pin 120 are enlarged like a rivet shape to sandwich the biological tissues L1 and L2. That is, each of both the ends of the pin 120 has a substantially T-shaped longitudinal cross section. Therefore, it is possible to maintain a state that the biological tissues L1 and L2 as welded targets are sandwiched and connected by bridging using the pins 120, and a state that the biological tissues L1 and L2 are appressed against each other can be maintained. Therefore, even if the connection portions of the biological tissues L1 and L2 are exposed to moisture, connection force (an appressed state) of the welded tissues L1 and L2 can be maintained.

Therefore, each pin 120 plays a role of pulling the biological tissues L1 and L2 close to each other and maintaining the appressed state even if the interface (connection surfaces) of the biological tissues L1 and L2 is exposed to the moisture. Therefore, a mutual network of the biological tissues L1 and L2 appressed against each other can be produced, tissue regeneration force of the biological tissues L1 and L2 can be easily exercised, and the biological tissues L1 and L2 can be regenerated on an earlier stage.

For example, after elapse of a predetermined time t2, the control unit 22 of the energy source 14 generates sound from the speaker 30 and stops the supply of the energy to the heat generation members 72 and 74. Further, the control unit 22 displays in the display unit 28 information indicating that the supply of the energy to the heat generation members 72 and 74 is stopped.

Furthermore, the pressed state of the pedal 16a of the foot switch 16 is released, the opening/closing lever 46a of the operation portion 46 is operated, the jaws 52 and 54 are opened, and the biological tissues L1 and L2 are released from the held state. It is to be noted that, if the pressed state of the pedal 16a of the foot switch 16 is released before the elapse of the predetermined time t2, the control unit 22 forcibly stops the supply of the energy to the heat generation members 72 and 74 from the heat generation member drive circuit 26.

It is to be noted that, since the pins 120 are absorbent members made of, e.g., magnesium or a magnesium alloy, they do not remain in a biological body forever, and they are absorbed into the biological tissues L1 and L2 and gradually decreased with time, and they eventually disappear. It is to be noted that a period from the moment of inserting the pins 120 so that the biological tissues L1 and L2 are appressed against each other to disappearance of the pins 120 differs depending on a length and a diameter of each pin, a state of the biological tissues L1 and L2, and others.

In this embodiment, although the description has been given as to the situation where the treatment instrument 12 is a bipolar type treatment instrument shown in FIG. 7A, the treatment instrument may be a monopolar type treatment instrument shown in FIG. 7B. In case of FIG. 7B, a treatment is given with a return electrode 66 attached to a patient P. That is, a treatment using the high-frequency electrodes 62 and 64 for the biological tissues L1 and L2 may be given by either the monopolar type instrument or the bipolar type instrument. Furthermore, when the treatment instrument 12 according to this embodiment is used as the monopolar type, the high-frequency energy may be supplied to only one of the high-frequency electrodes 62 and 64 arranged in the pair of jaws 52 and 54. It is to be noted that, like the states shown in FIG. 7A and FIG. 7B, using tabular heaters as the heat generation members 72 and 74 is also preferable. That is, it is also preferable to arrange the heat generation members 72 and 74 on the back surfaces of the electrodes 62 and 64.

In this embodiment, the description has been given as to the example where the openings 112 are formed in the electrode 62 arranged in the first jaw 52 and the concave portions 64a are formed in the electrode 64 arranged in the second jaw 54, but providing only one opening 112 and only one concave portion 64a is also preferable.

Further, although the description has been given as to the case where the openings 1120 are arranged in a line along the axial direction, the openings 112 may be arranged in a zigzag pattern or in multiple lines, e.g., two lines. In this case, the concave portions 64a of the electrode 64 are also formed in accordance with positions of the openings 112.

Moreover, in this embodiment, although the example using the pins 120 has been described, any other shape such as a coil-like shape may be adopted as long as the pins 120 can be stuck into the biological tissues L1 and L2.

A first modification of the first embodiment will now be described with reference to FIG. 8A and FIG. 8B. It is to be noted that, in this modification, like reference members denote members equal to those in the first embodiment or members having the same functions as much as possible, and a detailed description thereof will be omitted. This can be applied to not only the first modification of the first embodiment but also second to fifth modifications and a second embodiment explained below.

Figures 8A, 8B:
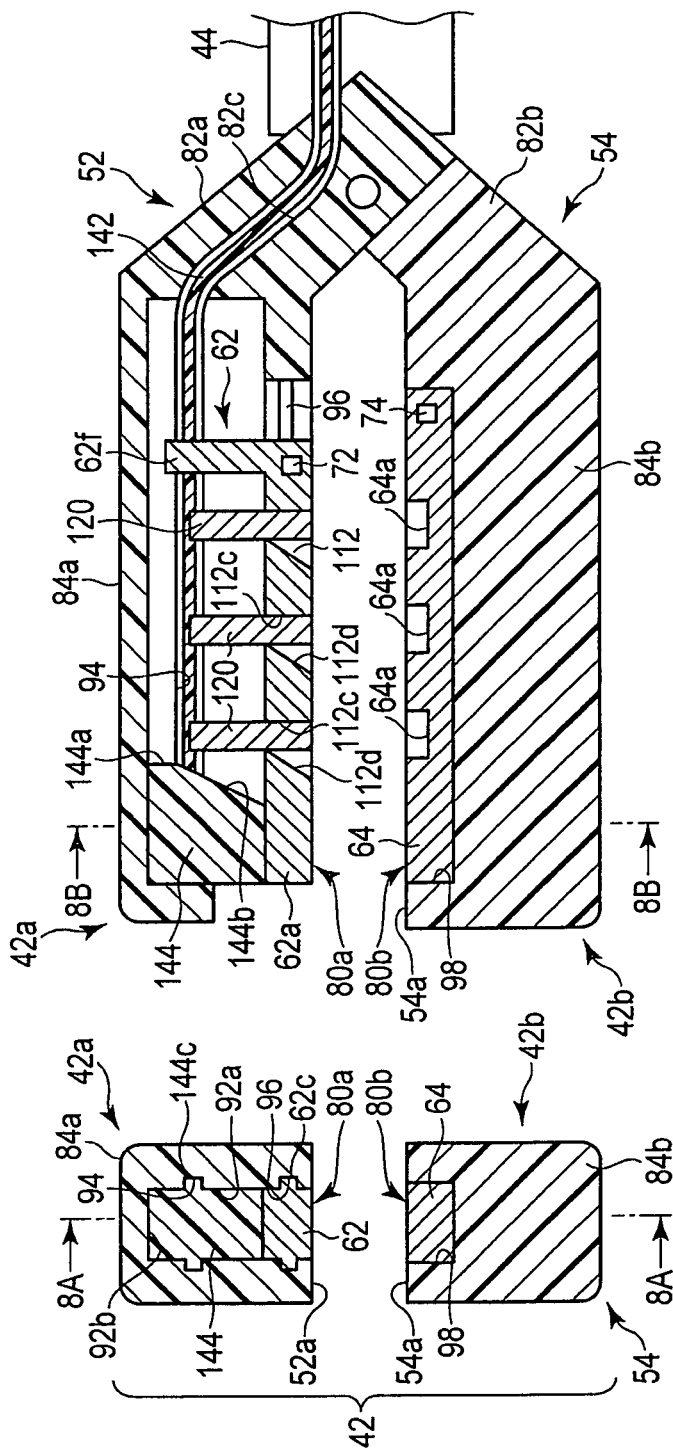
FIG. 8A is a schematic longitudinal cross-sectional view taken along a line 8A-8A in FIG. 8B, showing a treatment portion of a treatment instrument in an energy treatment system according to a first modification of the first embodiment.
FIG. 8B is a schematic transverse cross-sectional view taken along a line 8B-8B in FIG. 8A, showing the treatment portion of the treatment instrument in the energy treatment system according to the first modification of the first embodiment.

In the first modification, as shown in FIG. 8A, the pin 120 are arranged in the magazine 86 of the first jaw 52, and the slider 104 is arranged on the distal end side of the first jaw 52 before a puncture is made in the biological tissues L1 and L2. In this modification, in place of moving the slider 104 from the proximal end side to the distal end side of the first jaw 52 by using the pusher 102, a slider 144 is moved from the distal end side to the proximal end side of the first jaw 52 by using a pulling member 142 as a drive member formed of, e.g., a wire. That is, the pulling member 142 can be pulled by operating the slide lever 46b in the operation portion 46, and the slider 144 is fixed at the distal end of the pulling member 142.

It is to be noted that the slider 144 has an contact surface 144a and an inclined surface 144b on a proximal end surface thereof and it is arranged to be slidable between the bottom surface 92b of the substantially U-shaped extended portion 84 of the first jaw 52 and the back surface of the tabular portion 62a of the electrode 62. It is preferable for a normal line of the abutting surface 144a of the slider 144 to be parallel to the axial direction of, the insertion portion 44 or the extending direction (the longitudinal direction) of the extended portion 84a of the first jaw 52, and a normal line of the inclined surface 144b is inclined with respect to the axial direction of the insertion portion 44 or the extending direction (the longitudinal direction) of the extended portion 84a of the first jaw 52 and directed to the back surface of the tabular portion 62a of the electrode 62. Furthermore, each convex portion 144c that is slidably engaged with the groove portion 94 is formed in the slider 144.

When the pulling member 142 is pulled and retracted, the contact surface 144a of the slider 144 is allowed to come into contact with the stand-up portion 62f at the proximal end of the electrode 62. When the pulling member 142 is further retracted, since the stand-up portion 62f of the electrode 62 is pressed toward the proximal end of the first jaw 52 by using the contact surface 144a of the slider 144, the electrode 62 can be moved toward the proximal end of the first jaw 52.

Opening portions 112 each of which is formed into an oval shape that is long in the longitudinal direction of the first jaw 52 on the surface side (a side facing the electrode 64 arranged in the second jaw 54) and formed into a circular shape on the back surface side (a side facing the bottom surface 92b of the extended portion 84) are formed in the tabular portion 62a of the electrode 62 at appropriate intervals. A circumferential length of each opening 112 in the board thickness direction of the tabular portion 62a of the electrode 62 is formed to be gradually shortened from the surface side toward the back surface side of the tabular portion 62a. Each opening 112 on the proximal end side of the first jaw 52 is formed into a surface (an orthogonal surface) 112c orthogonal to the axial direction, and the same on the distal end side is formed into an inclined surface 112d. A normal line of the inclined surface 112d is directed toward the electrode 64 of the second jaw 54.

A brief description will now be given as to an operation of the treatment system 10 according to the first modification to apply energy to the biological tissues L1 and L2 as fusion targets and give a treatment to the biological tissues.

After the biological tissues L1 and L2 are denatured by using the high-frequency electrodes 62 and 64, when the slide lever 46b in the operation portion 46 is operated and the slider 144 is pulled by the pulling member 142, the pins 120 are pressed by the inclined surface 144b of the slider 144 and sequentially stuck into the biological tissues from the distal end side toward the proximal end side. When the contact surface 144a of the slider 144 is allowed to come into contact with the stand-up portion 62f at the rear end of the electrode 62, the electrode 62 moves from the distal end side toward the proximal end side of the first jaw 52. With the movement of the electrode 62, the pins 120 are pressed by the inclined surfaces 112d and further stuck into the biological tissues, and the lower ends of the pins 120 reach the concave portions 64a of the electrode 64 arranged in the second jaw 54.

Any other function has been explained in the first embodiment, a description thereof will be omitted here.

It is to be noted that the description has been given as to the example where the pulling member 142 is used as the drive member formed of, e.g., wire in this modification, the pulling member 142 may be a plate-like member, e.g., the pusher 102 explained in the first embodiment besides the wire. That is, the pusher 102 explained in the first embodiment may be used as the pulling member.

A second modification of the first embodiment will now be described with reference to FIG. 9A and FIG. 9B.

As shown in FIG. 9A, this modification is an example where the first jaw 52 and the electrode 62 of the first holding portion 42a and the second jaw 54 and the electrode 64 of the second holding portion 42b are moved from the distal end side toward the proximal end side. Specifically, the base portion 82a and the extended portion 84a of the first jaw 52 are separately formed, and the extended portion 84a can move in the axial direction with respect to the base portion 82a. Likewise, the base portion 82b and the extended portion 84b of the second jaw 54 are separately formed, and the extended portion 84b can move in the axial direction with respect to the base portion 82b. Moreover, pulling members 152 and 154, e.g., wires as drive members are arranged between the operation portion 46 and the extended portions 84a and 84b of the first and second jaws 52 and 54 through the insertion portion 44.

It is to be noted that, e.g., oval openings 162a and 162b are formed in the extended portions 84a and 84b, and protrusions 164a and 164b that engage with the openings 162a and 162b are formed on the base portions 82a and 82b. Therefore, when the extended portions 84a and 84b are pulled toward the proximal end side by the pulling members 152 and 154, the protrusions 164a and 164b of the base portions 82a and 82b move in the oval openings 162a and 162b of the extended portions 84a and 84b. That is, the movement of the extended portions 84a and 84b with respect to the base portions 82a and 82b is restricted to a predetermined range by the openings 162a and 162b and the protrusions 164a and 164b.

Therefore, when the pulling members 152 and 154 are operated to be pulled by using the operation portion 46, the extended portion 84a of the first jaw 52 can be moved toward the proximal end side with respect to the base portion 82a of the first jaw 52, and the extended portion 84b of the second jaw 54 can be moved toward the proximal end side with respect to the base portion 82b of the second jaw 54.

In case of moving the extended portion 84a of the first jaw 52 toward the proximal end side with respect to the base portion 82a of the first jaw 52 and in case of moving the extended portion 84b of the second jaw 54 to the proximal end side with respect to the base portion 82b of the second jaw 54, the heat generation member drive circuit 26 is driven, and the heat generation members 72 and 74 are allowed to generate heat. Additionally, the heat is transferred to the biological tissues and the end portions of the pins 120 from the heat generation members 72 and 74 through the electrodes 62 and 64, and the end portions of the pins 120 are heated to a predetermined temperature or a higher temperature.

In this modification, the extended portions 84a and 84b of the first and second jaws 52 and 54 move toward the side close to the operation portion 46. Therefore, when the extended portions 84a and 84b of the jaws 52 and 54 are relatively moved while heating the pins 120 as shown in FIG. 9B, both the end portions of the pins 120 can be bent. When heating the heat generation members 72 and 74 by using the heat generation member drive circuit 26 is stopped, the end portions of the pins 120 are hardly further deformed, and hence a state that the biological tissues L1 and L2 are connected by bridging using the pins 120 can be maintained.

A third modification of the first embodiment will now be explained with reference to FIG. 10A and FIG. 10B, and this modification is a modification of the second modification.

As shown in FIG. 10A, this modification is an example where the extended portion 84a and the electrode 62 (and the heat generation member 72) of the first jaw 52 are moved to the distal end side, and the extended portion 84b and the electrode 64 (and the heat generation member 74) of the second jaw 54 are moved to the proximal end side. A pressing member 172, e.g., a pusher as a drive member is arranged between the operation portion 46 and the extended portion 84a of the first jaw 52 through the insertion portion 44. A pulling member 174, e.g., a wire as a drive member is arranged between the operation portion 46 and the extended portion 84b of the second jaw through the insertion portion 44.

Therefore, when the pressing member 172 is operated to be pressed out by using the operation portion 46, the extended portion 84a of the first jaw 52 can be moved toward the distal end side with respect to the base portion 82a of the first jaw 52. On the other hand, when the pulling member 174 is operated to be pulled by using the operation portion 46, the extended portion 84b of the second jaw 54 can be moved to the proximal end side with respect to the base portion 82b of the second jaw 54.

In case of moving the extended portion 84a of the first jaw 52 to the distal end side with respect to the base portion 82a of the first jaw 52 and in case of moving the extended portion 84b of the second jaw 54 to the proximal end side with respect to the base portion 82b of the second jaw 54, the heat generation member drive circuit 26 is driven, the heat generation members 72 and 74 are allowed to generate heat, and the heat is transferred to the biological tissues L1 and L2 and the end portions of the pins 120 through the electrodes 62 and 64, whereby the end portions of the pins 120 are bent as shown in FIG. 10B. Therefore, a state that the biological tissues L1 and L2 are connected by bridging is maintained.

That is, in this modification, the extended portion 84a of the first jaw 52 moves away from the operation portion 46, and the extended portion 84b of the second jaw 54 moves closer to the operation portion 46. Therefore, when the extended portions 84a and 84b of the first and second jaws 52 and 54 are relatively moved as shown in FIG. 12B while heating the pins 120, both the ends of the pins 120 can be bent in opposite directions.

A fourth modification of the first embodiment will now be described with reference to FIG. 11A to FIG. 13.

This modification is an example using a surgical staple 180 which can be deformed when it is heated to a predetermined temperature or a high temperature, has biocompatible properties and bioabsorbable properties, and is a substantially U-shaped staple of a stapler in place of the pin 120.

Figure 11A:
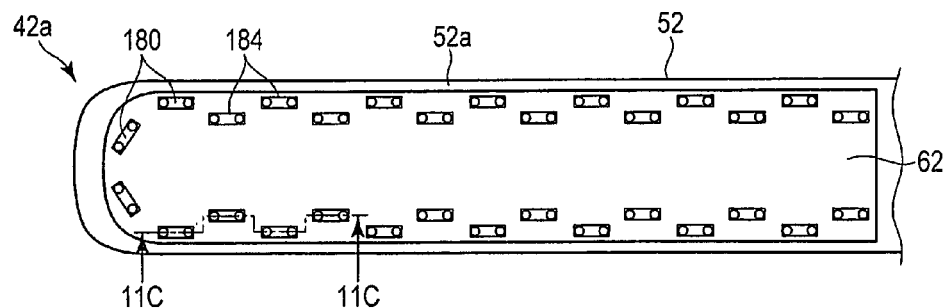
FIG. 11A is a schematic view showing a treatment portion of a treatment instrument in an energy treatment system according to a fourth modification of the first embodiment when an electrode arranged in a first jaw is seen from an electrode arranged in a second jaw.
Figure 11B:
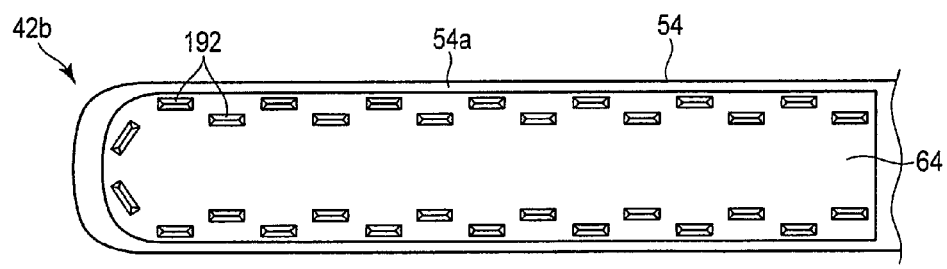
FIG. 11B is a schematic view showing the treatment portion of the treatment instrument in the energy treatment system according to the fourth modification of the first embodiment when the electrode arranged in the second jaw is seen from the electrode arranged in the first jaw.
Figure 11C:
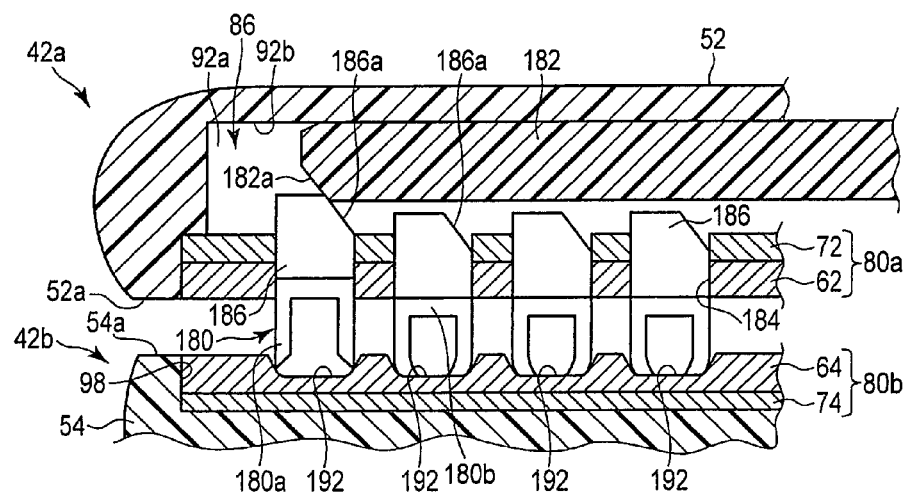
FIG. 11C is a schematic longitudinal cross-sectional view taken along a line 11C-11C in FIG. 11A, showing the treatment portion of the treatment instrument in the energy treatment system according to the fourth modification of the first embodiment.

As shown in FIG. 11A and FIG. 11C, the staples 180 are arranged in the magazine 86 between the first jaw 52 and the back surface of the electrode 62. As shown in FIG. 11A and FIG. 11B, in this modification, the staples 180 are arranged near the edge portion of the electrode 62, arranging the staples 180 at the center is also preferable.

As shown in FIG. 11A, a pusher rod 182 having an inclined surface 182a is accommodated to arrow its forward and backward movement in a magazine 86, which is configured to discharge the surgical staples (absorbent members) 180, in the extended portion 84a of the first jaw 52. The staples 180 are accommodated in the magazine 86, each has a pair of leg portions 180a and an arm 180b that connects the leg portions 180a in such a manner that the leg portions 180a face the electrode 64 arranged in the second jaw 54 and the leg portions 180a of the staples 180 can protrude in the direction of the surface of the electrode 64 of the second jaw 54. Guide grooves (openings) 184 are formed in the electrode 62 and the heat generation member 72 to face the pusher rod 182. Staple pushers 186 each having an inclined surface 186a which is inclined like the inclined surface 182a of the pusher rod 182 are arranged in the guide grooves 184 to be slidable with respect to the guide grooves 184.

As shown in FIG. 11B and FIG. 11C, staple deformation grooves 192 are formed in the surface (a holding surface) of the electrode 64 arranged in the second jaw 54. Each staple deformation groove 192 has a bottom surface formed into, e.g., an arc shape so that a pair of leg portions 180a (see FIG. 11C) of each staple 180 can be inwardly bent and deformed while being heated. Therefore, the surface of the electrode 64 arranged in the second jaw 54 also has a function as an anvil of the staple 180.

It is to be noted that each guide groove 184 shown in FIG. 11A and each staple deformation groove 192 shown in FIG. 11B are formed at positions where they face each other.

As shown in FIG. 12, the treatment instrument 12 includes a motor (a drive source) 196 such as a linear motor. Although the motor 196 may be arranged in any one of the operation portion 46, the insertion portion 44, and the first jaw 52 of the treatment instrument 12, a description will be given on the assumption that the motor 196 is arranged in the operation portion 46 in this modification. Further, the motor 196 is connected to the control unit 22 of the energy source 14. The control unit 22 can determine a position of the pusher rod 182 by controlling the motor 196. Therefore, a discharge state of the staples 180 with respect to the first jaw 52 can be detected.

A function of the treatment system 10 according to this modification will now be described.

As described in the first embodiment, the biological tissues L1 and L2 as treatment targets are held between the electrode 62 arranged in the first jaw 52 and the electrode 64 arranged in the second jaw 54, and the pedal 16a of the foot switch 16 is pressed down. Therefore, the biological tissues L1 and L2 between the electrodes 62 and 64 are heated by using an output from the high-frequency energy output circuit 24, the biological tissues L1 and L2 are denatured by the thermal energy, and the output from the high-frequency energy output circuit 24 is stopped after, e.g., a predetermined time t1 passes.

Then, the pressed state of the pedal 16a of the foot switch 16 is kept, the motor 196 is automatically driven while heating the electrodes 62 and 64 with use of the heat generation members 72 and 74, and the pusher rod 182 slowly moves forward. When the pusher rod 182 slowly moves, the inclined surfaces 186a of the staple pushers 186 slidably arranged in the guide grooves 184 are pressed down by the inclined surface 182a at the distal end of the pusher rod 182. Therefore, as shown in FIG. 11C, the staple pushers 186 move along the guide grooves 184 from the back surface side to the top surface side of the electrode 62 arranged in the first jaw 52.

Therefore, the staples 180 protrude from the magazine 86 of the first jaw 52, and they are driven into the target tissues L1 and L2. A pair of leg portions 180a of each of the driven staples 180 penetrate through the biological tissues L1 and L2. Furthermore, since these leg portions 180a are heated by the heat of the electrode 64 transferred from the heat generation member 74 of the second jaw 54, they are inwardly bent by the staple deformation grooves 192 provided on the surface of the electrode 64 arranged in the second jaw 54. Therefore, the biological tissues L1 and L2 as the fusion targets are connected by the staples 180.

It is to be noted that the heat generation member 74 arranged in the second jaw 54 is allow to generate heat and to deform a pair of leg portions 180a of each of the staples 180 through the electrode 64 and, at the same time, the biological tissues L1 and L2 held between the electrodes 62 and 64 are dehydrated. On the other hand, when the heat generation member 72 arranged in the first jaw 52 is allowed to generate heat, the biological tissues L1 and L2 held between the electrodes 62 and 64 are dehydrated through the electrode 62. Therefore, for example, since an amount of moisture in the interface of the biological tissues L1 and L2 can be reduced, the biological tissues L1 and L2 can be connected with the increased connection force, and these tissues are connected while they are discretely mechanically connected by bridging.

Additionally, when the supply of the energy from the heat generation member drive circuit 26 to the heat generation member 72 arranged in the first jaw 52 and the heat generation member 74 arranged in the second jaw 54 is stopped, the leg portions 180a of the staples 180 are cooled from a temperature that enables deformation to a temperature that hardly enables deformation, and the deformed state is maintained.

That is, as shown in FIG. 13, the control unit 22 of the energy source 14 can control to enable output of the energy from the high-frequency energy output circuit 24 and the heat generation member drive circuit 26. Therefore, after the biological tissues L1 and L2 are held between the electrodes 62 and 64, when the pressed state of the pedal 16a of the foot switch 16 is maintained, a series of connection treatments of the biological tissues L1 and L2 (the connection of the biological tissues L1 and L2 between the electrodes 62 and 64 using the high-frequency energy, and the dehydration of the biological tissues L1 and L2 between the electrodes 62 and 64 heated by the heat transfer from the heat generation members 72 and 74 using the thermal energy) can be automatically carried out.

In this modification, the leg portions 180a of the staples 180 can be gradually deformed while waiting for a temperature of the leg portions 180a of the staples 180 to increase to a temperature that enables deformation, and the biological tissues L1 and L2 can be connected by bridging using the staples 180.

It is to be noted that the motor 196 does not have to be necessarily used, and an operator may operate the slide lever 46b of the operation portion 46 and slowly move forward the pusher rod 182.

A fifth modification of the first embodiment will now be described with reference to FIG. 14 to FIG. 15B.

Although the description has been given as to the example where the leg portions 180a of the staples 180 are heated and bent in the staple deformation grooves 192 on the surface of the electrode 64 arranged in the second jaw 54 in the fourth modification, pointed end portions 180c of the leg portions 180a can be allowed to abut on concave portions 64b on the surface of the electrode 64 in this modification. In this case, the heat generation member 74 does not have to generate heat at the same time with the forward movement of the pusher rod 182, the pointed end portions 180c of the leg portions 180a of the staples 180 can be allowed to abut on the concave portions 64b of the electrode 64, then the heat generation member 74 can be allowed to generate heat with the pointed end portions 180c of the leg portions 180a of the staples 180 abutting on the concave portions 64b of the electrode 64, and the pointed end portions 180c of the leg portions 180a of the staples 180 can be heated. Therefore, when a position of the pusher rod 182, e.g., end of the forward movement of the pusher rod 182 is detected instead of detecting formation of a closed circuit as described above, the control unit 22 can output the energy to the heat generation members 72 and 74 from the heat generation member drive circuit 26 in place of outputting the energy to the electrodes 62 and 64 from the already stopped high-frequency energy output circuit 24. That is, when a state of the motor 196 is detected and the discharge of the staples (the absorbent members) 180 from the first jaw 52 is detected, the control unit 22 controls the energy source 14 and changes the high-frequency energy supply state to the thermal energy supply state. Subsequently, the energy is output from the heat generation member drive circuit 26, and the heat generation members 72 and 74 are allowed to generate heat. Then, the pointed end portions 180c of the leg portions 180a of the staples 180 are enlarged and deformed, and the biological tissues L1 and L2 can be bridged between the pointed end portions 180c and each arm 180b.

A sixth modification of the first embodiment will now be described with reference to FIG. 16A to FIG. 16E. This modification is a further modification of the fourth and fifth modifications.

For example, a staple receiving portion 190 shown in FIG. 16A is arranged in each concave portion 64b of the electrode 64 arranged in the second jaw 54. This staple receiving portion 190 is made of a bioabsorbable material. The staple receiving portion (an absorbent member) 190 may be made of the same material as the staple 180 or may be made of a different material. For example, a magnesium allow is used for the staple 180, the staple receiving portion 190 may be made of the same magnesium alloy.

The staple receiving portion 190 includes ring portions 190a into which a pair of pointed end portions 180c of the staple 180 can be inserted and a coupling portion 190b connecting these ring portions 190a. Here, an opening width l of an opening portion 190c of each ring portion 190a is formed larger than a width a of the pointed end portion 180c of the staple 180. Therefore, as shown in FIG. 16B, each pointed end portion 180c of the staple 180 can be inserted into the opening portion 190c of each ring portion 190a.

It is to be noted that the staple receiving portion 190 is arranged on the electrode 64 provided in the second jaw 54 in such a manner that the pointed end portions 180c of each pair of leg portions 180a of the staples 180 driven from the first jaw 52 can be inserted into the opening portions 190c of the ring portions 190a of the staple receiving portions 190.

A function of the treatment system 10 according to this modification will now be described.

Although not shown, as described in the first embodiment, the biological tissues L1 and L2 as treatment targets are held between the electrode 62 arranged in the first jaw 52 and the electrode 64 provided in the second jaw 54. At this time, each staple receiving portion 190 arranged on the electrode 64 arranged in the second jaw 54 is appressed against the biological tissue L2.

In this state, the pedal 16a of the foot switch 16 is pressed down. Therefore, the biological tissues L1 and L2 between the electrodes 62 and 64 are heated by using an output from the high-frequency energy output circuit 24, the biological tissues L1 and L2 are denatured by the thermal energy, and the output from the high-frequency energy output circuit 24 is stopped after elapse of, e.g., a predetermined time t1.

Then, when the pressed state of the pedal 16a of the foot switch 16 is maintained, the staples 180 protrude as described above, and they are driven into the target tissues L1 and L2. As shown in FIG. 16C, each pair of leg portions 180a of the driven staples 180 pierce through the biological tissues L1 and L2, and they are inserted into the respective ring portions 190a of the staple receiving portions 190 arranged on the concave portions 64b of the electrode 64 arranged in the second jaw 54. Further, as described in the fifth modification, the heat is generated in the heat generation member 74 with the pointed end portions 180c of the leg portions 180a of the staples 180 abutting on the concave portions 64b of the electrode 64, and the pointed end portions 180c of the leg portions 180a of the staples 180 are heated.

Therefore, as shown in FIG. 16D and FIG. 16E, the pointed end portions 180c of the leg portions 180a of the staples 180 are enlarged and deformed, and the biological tissues L1 and L2 can be bridged between the pointed end portions 180c and the arms 180b.

It is to be noted that, in each of the fourth to sixth modifications, the heat generation member 72 arranged in the first jaw 52 does not have to be necessarily provided or allowed to generate heat. That is, the arms 180b of the staples 180 do not have be necessarily heated and deformed. When the pointed end portions 180c of each pair of leg portions 180a of the staples 180 are inwardly bent or deformed to be enlarged, the biological tissues L1 and L2 can be held between each pair of leg portions 180a and each arm 180b.

A second embodiment will now be described with reference to FIG. 17A to FIG. 17F.

Figure 17A:
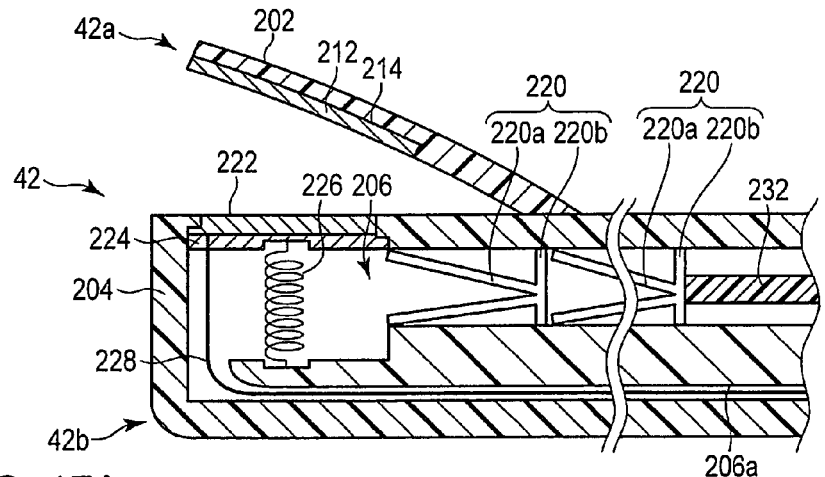
FIG. 17A is a schematic longitudinal cross-sectional view showing a treatment portion of a treatment instrument in an energy treatment system according to a second modification.

As shown in FIG. 17A, a treatment portion 42 of a treatment instrument 12 according to this embodiment includes a pair of openable and closable jaws (first and second jaws) 202 and 204. In this embodiment, a description will be given as to an example where the second jaw 204 on the lower side in FIG. 17A is fixed and the first jaw 202 on the upper side is relatively opened or closed with respect to the second jaw 204 on the lower side. It is to noted that, when an opening/closing lever 46a (see FIG. 1) of an operation portion 46 is operated, the first jaw 202 can be opened/closed with respect to the second jaw 204.

The first jaw 202 includes an electrode 212 arranged on a holding surface to hold a biological tissue and a heat generation member 214 that transfers heat to the electrode and dehydrates the biological tissue by using thermal energy. The heat generation member 214 is arranged on a side surface or a back surface of the electrode 212. It is to be noted that the electrode 212 is connected to a high-frequency energy output circuit 24 in FIG. 2, and the heat generation member 214 is connected to a heat generation member drive circuit 26 in FIG. 2.

Absorbent members 220 which are made of, e.g., a magnesium alloy and have bioabsorbable properties are aligned in a magazine 206 of the second jaw 204 along an axial direction. Each absorbent member 220 includes a clip portion 220a having a substantially V-shaped longitudinal cross section and a base portion (a stand-up portion) 220b. Like the pin 120 or the surgical staple 180 explained in the first embodiment, the absorbent member 220 can be deformed when heated, and it is absorbed into a biological tissue with time.

A lifter electrode 222 of which a heat generation member 224 and an elastic member 226 such as a coil spring are arranged on a back surface is arranged in the second jaw 204. It is to be noted that the electrode 222 is connected to the high-frequency energy output circuit 24 depicted in FIG. 2, and the heat generation member 224 is connected to the heat generation member drive circuit 26 in FIG. 2. Therefore, when the biological tissues L1 and L2 are held between the electrodes 212 and 222, the biological tissues L1 and L2 can be connected by using the high-frequency energy based on an output from the high-frequency energy output circuit 24, and the biological tissues L1 and L2 can be dehydrated by using an output from the heat generation member drive circuit 26.

Figure 17B:
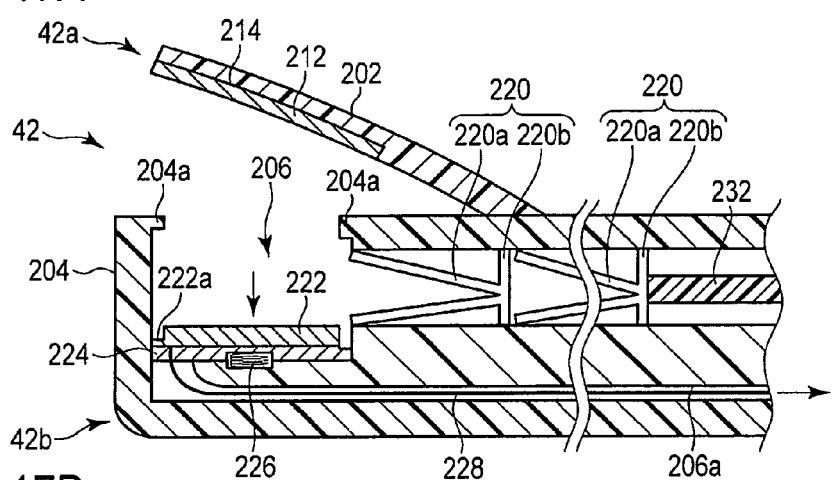
FIG. 17B is a schematic longitudinal cross-sectional view showing the treatment portion of the treatment instrument in the energy treatment system according to the second embodiment and also showing an operation following FIG. 17A.

As shown in FIG. 17B, in this embodiment, an engagement portion 222a that can engage with an engagement portion 204a of the second jaw 204 is formed in the lifter electrode 222. Furthermore, as shown in FIG. 17A, it is preferable for a biological tissue holding surface which is a surface of the lifter electrode 222 to be flush with the biological tissue holding surface of the second jaw 204.

A distal end of a pulling member 228 such as a wire is connected to the back surface of the lifter electrode 222. A proximal end of this pulling member 228 is extended toward an operation portion 46 along a duct 206a extended in the axial direction of the second jaw 204. When a slide lever 46b (see FIG. 1) of the operation portion 46 is operated, this pulling member 228 can be operated. It is to be noted that an inner peripheral surface of the jaw 204 at the distal end functions as a guide for the lifter electrode 222.

The absorbent members 220 are aligned in the magazine 206 of the lower jaw 204 along the axial direction. Here, in each absorbent member 22, an opened side of the clip portion 220a is provided on a distal end side, and the base portion 220b is provided on a proximal end side (the opened side of the clip 220a of a subsequent absorbent member 220). A distal end of a pusher rod 232 is arranged at the proximal end of the absorbent member 220 on the outermost proximal end side so that the pusher rod 232 can press the proximal end. A proximal end of the pusher rod 232 can be operated in, e.g., the operation portion 46 or the proximal end portion of the insertion portion 44 along the axial direction.

A function of an energy treatment system 10 having the treatment instrument 12 according to this embodiment will now be described.

As shown in FIG. 17A, the lifter electrode 222 is moved up to put a lid on the holding surfaces for the biological tissues L1 and L2. Further, the biological tissues are held by the pair of jaws 202 and 204, the high-frequency energy is output to the biological tissues to denature the biological tissues L1 and L2, and the biological tissues L1 and L2 are connected.

The biological tissues L1 and L2 connected by applying the high-frequency energy are released once, the slide lever 46b of the operation portion 46 is operated, the pulling member 228 is pulled as shown in FIG. 17B, and the lifter electrode 222 is moved down against biasing force of the elastic member 226. At this time, it is preferable to maintain the state of the pulling member 228 by using a well-known ratchet mechanism and the like. That is, the lifter electrode 222 is maintained at a position shown in FIG. 17B.

Figure 17C:
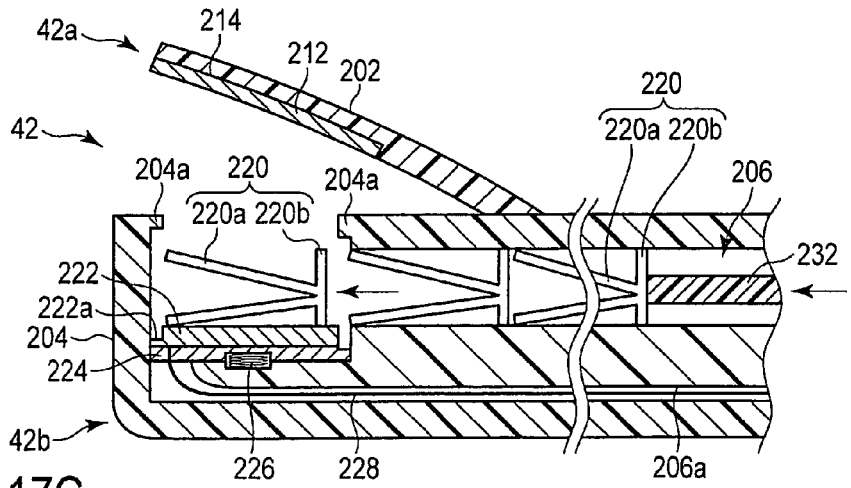
FIG. 17C is a schematic longitudinal cross-sectional view showing the treatment portion of the treatment instrument in the energy treatment system according to the second embodiment and also showing an operation following FIG. 17B.

As shown in FIG. 17C, the pusher rod 232 is operated to move to the distal end side of the lower jaw 204, and the distal end of the absorbent member 220 on the outermost distal end side is allowed to abut on the distal end of the magazine 206, and the absorbent member 220 on the outermost distal end side is mounted on the lifter electrode 222.

Figure 17D:
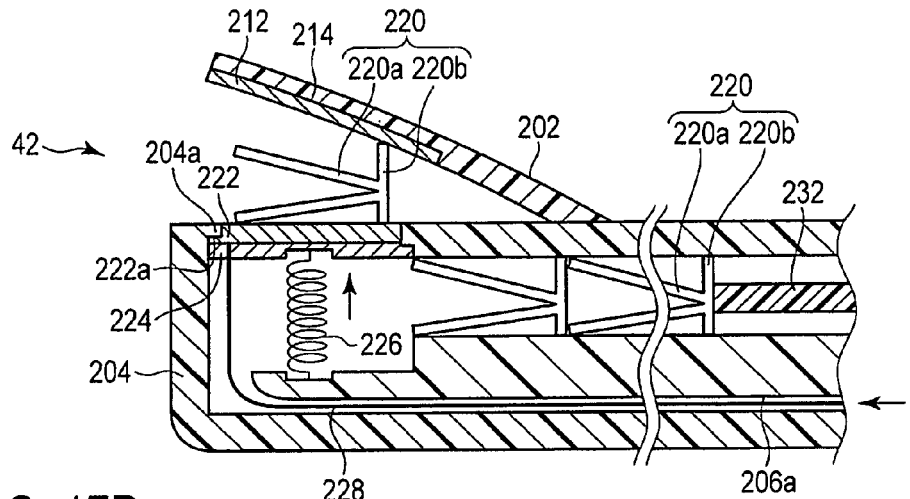
FIG. 17D is a schematic longitudinal cross-sectional view showing the treatment portion of the treatment instrument in the energy treatment system according to the second embodiment and also showing an operation following FIG. 17C.

When the slide lever 46b of the operation portion 46 is operated and the pulling member 226 is pressed toward the distal side or the ratchet mechanism is released, the lifter electrode 222 moves up by elastic force of the elastic member 226 as shown in FIG. 17D. At this time, the lifter electrode 222 is positioned when the engagement portion 222a of the lifter electrode 222 is caught by the engagement portion 204a of the jaw 204 at the distal end. The absorbent member 220 is arranged between the lifter electrode 222 of the second jaw 204 and the first jaw 202.

Figure 17E:
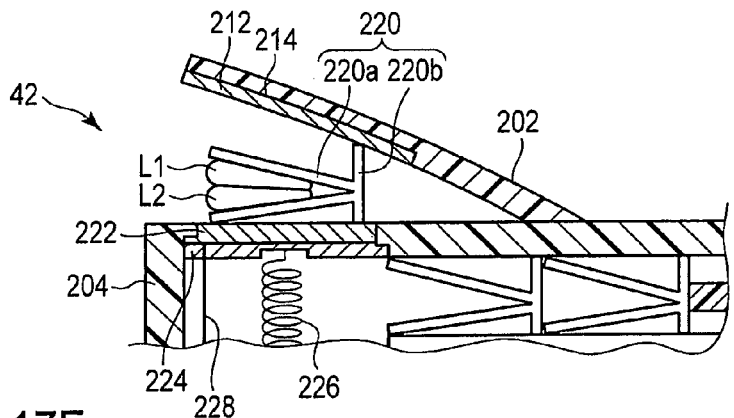
FIG. 17E is a schematic longitudinal cross-sectional view showing the treatment portion of the treatment instrument in the energy treatment system according to the second embodiment and also showing an operation following FIG. 17D.

As shown in FIG. 17E, in this state, the biological tissues L1 and L2 denatured by application of the high-frequency energy are held in the absorbent member 220.

Figure 17F:
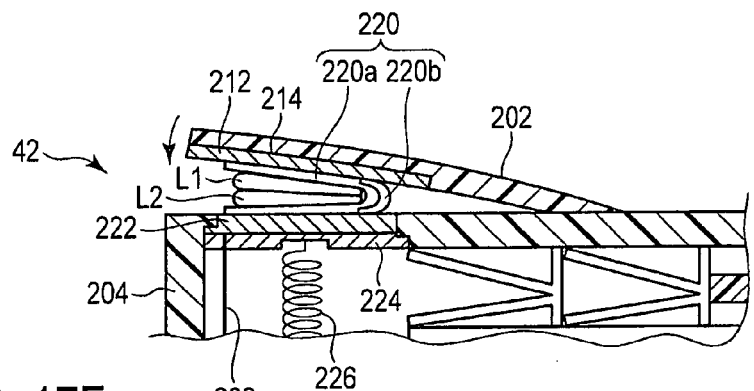
FIG. 17F is a schematic longitudinal cross-sectional view showing the treatment portion of the treatment instrument in the energy treatment system according to the second embodiment and also showing an operation following FIG. 17E.

Further, the heat generation members 214 and 224 are heated, and the first jaw 202 is relatively closed with respect to the second jaw 204 as shown in FIG. 17F. At this time, the base portion 220b of the absorbent member 220 is heated and deformed, and the clip portion 220a is also heated and deformed. In this manner, after the first jaw 202 is relatively closed with respect to the second jaw 204, heating of the heat generation member 224 is stopped. Since the base portion 220b of the absorbent member 220 is solidified in a deformed state, the biological tissues L1 and L2 are maintained while being held by the absorbent member 220.

Although not shown, the upper jaw 202 is opened with respect to the lower jaw 204, and the biological tissues L1 and L2 held by the absorbent member 220 are released.

Therefore, a state that the biological tissues L1 and L2 as fusion targets are held by the absorbent member 220 and connected by bridging can be maintained, and a state that the biological tissues L1 and L2 are appressed against each other can be maintained. Therefore, even if the connected portions of the biological tissues L1 and L2 are exposed to moisture, connection force (the appressed state) of the connected tissues L1 and L2 can be maintained.

It is to be noted that, in case of continuously giving the same treatment, a series of operations shown in FIG. 17A to FIG. 17F are again performed. At this time, as shown in FIG. 17C, when the pusher rod 232 is operated and the absorbent member 220 is mounted on the lifter electrode 222, the same treatment can be given, and hence the treatment instrument 12 according to this embodiment can be preferably used when the same treatment is given to more than one position.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment system configured to apply energy to biological tissues as fusion targets and give a treatment to the biological tissues, comprising:
    an energy source which is configured to generate high-frequency energy and thermal energy;
    an insertion portion which includes a distal end portion, a proximal end portion, and a longitudinal direction defined by the distal end portion and the proximal end portion, and which is extended from the proximal end portion toward the distal end portion along the longitudinal direction;
    a first jaw which is provided at the distal end portion of the insertion portion and includes a first holding surface;
    a second jaw which is provided at the distal end portion of the insertion portion, and which includes a second holding surface that faces the first holding surface and that is configured to hold the biological tissues as the fusion targets in cooperation with the first holding surface;
    an absorbent member which is arranged to be discharged into the biological tissues as the fusion targets from the first jaw through the first holding surface, thermally deformed when the thermal energy is applied thereto, and configured to be absorbed into the biological tissues as the fusion targets with time while being arranged in the biological tissues as the fusion targets;
    a drive member which is inserted into the insertion portion and the first jaw and that is configured to move with respect to the insertion portion;
    a first energy discharge portion which is slidable, with respect to the first jaw, depending on a movement of the drive member, along the longitudinal direction, which is configured to discharge the absorbent member toward the second holding surface through the first holding surface when it slides along the longitudinal direction, and which is configured to supply the high-frequency energy and the thermal energy to the biological tissues;

a second energy discharge portion which is provided on the second holding surface, which is configured to come into contact with at least a part of the absorbent member when the absorbent member is discharged, and which is configured to supply the high-frequency energy and the thermal energy to the biological tissues; and a control unit which is configured to control the energy source to enable application of the high-frequency energy and the thermal energy to the biological tissues as the fusion targets in the mentioned order through at least one of the first energy discharge portion and the second energy discharge portion, and which is configured to control the energy source to supply the thermal energy after discharging the absorbent member to the biological tissues, wherein:

the first energy discharge portion comprises an opening through which the absorbent member is configured to protrude from the first holding surface; and the first energy discharge portion is used as an electrode that is configured to supply the high-frequency energy and the thermal energy to the biological tissues.

2. The treatment system according to claim 1, wherein the absorbent member has conductive properties, and the control unit is configured to control the energy source to supply the thermal energy when the first energy discharge portion and the second energy discharge portion are conducted through the absorbent member after at least part of the absorbent member comes into contact with the second energy discharge portion while at least a part of the absorbent member comes into contact with the first energy discharge portion.

3. The treatment system according to claim 2, wherein the control unit is configured to stop the supply of the high-frequency energy configured to treat the biological tissues before discharging the absorbent member.

4. The treatment system according to claim 1, further comprising:

a pusher rod which is configured to discharge the absorbent member; and a drive source which is configured to move the pusher rod and which is connected to the control unit, wherein the control unit is configured to control the energy source to supply the thermal energy when a state of the drive source is detected and discharge of the absorbent member from the pusher rod is detected.

5. The treatment system according to claim 1, wherein at least one of the first and second energy discharge portions includes a resistive heater configured to apply the thermal energy to the absorbent member.

6. The treatment system according to claim 1, wherein the absorbent member is made of a magnesium alloy.

7. The treatment system according to claim 1, wherein the absorbent member is arranged to clip the biological tissues when the thermal energy is supplied thereto from at least one of the first and second energy discharge portions.

8. The treatment system according to claim 1, wherein the absorbent member is formed to be stuck into the biological tissues as the fusion targets, and the second jaw includes a receiving portion that receives the bioabsorbable member arranged to connect the biological tissues as the fusion targets.

9. A treatment device configured to apply energy to biological tissues as fusion targets and give a treatment to the biological tissues, comprising:

an insertion portion which includes a distal end portion, a proximal end portion, and a longitudinal direction defined by the distal end portion and the proximal end portion, and which is extended from the proximal end portion toward the distal end portion along the longitudinal direction;

a first jaw which is provided at the distal end portion of the insertion portion and includes a first holding surface;

a second jaw which is provided at the distal end portion of the insertion portion, and which includes a second holding surface that faces the first holding surface and that is configured to hold the biological tissues as the fusion targets in cooperation with the first holding surface;

an absorbent member which is arranged to be discharged into the biological tissues as the fusion targets from the first jaw through the first holding surface, thermally deformed when thermal energy generated by an energy source is applied thereto, and configured to be absorbed into the biological tissues as the fusion targets with time while being arranged in the biological tissues as the fusion targets;

a drive member which is inserted into the insertion portion and the first jaw and that is configured to move with respect to the insertion portion;

a first energy discharge portion which is slidable, with respect to the first jaw, depending on a movement of the drive member, along the longitudinal direction, which is configured to discharge the absorbent member toward the second holding surface through the first holding surface when it slides along the longitudinal direction, and which is configured to supply high-frequency energy generated by the energy source and the thermal energy to the biological tissues; and a second energy discharge portion which is provided on the second holding surface, which is configured to come into contact with at least a part of the absorbent member when the absorbent member is discharged, and which is configured to supply the high-frequency energy and the thermal energy to the biological tissues, wherein:

the first energy discharge portion comprises an opening through which the absorbent member is configured to protrude from the first holding surface; and the first energy discharge portion is used as an electrode that is configured to supply the high-frequency energy and the thermal energy to the biological tissues.

* * * * *

UNITED STATES PATENT AND TRADEMARK OFFICE
CERTIFICATE OF CORRECTION

Page 1 of 1

PATENT NO. : 9,125,663 B2
APPLICATION NO. : 13/668861
DATED : September 8, 2015
INVENTOR(S) : Hiroaki Ichikawa et al.

It is certified that error appears in the above-identified patent and that said Letters Patent is hereby corrected as shown below:

On The Title Page, Item (71), Applicant, change "Olympus Medical Systems Corp., Tokyo (JP)" to
-- Olympus Corporation, Tokyo (JP) --.

Signed and Sealed this
Twenty-ninth Day of March, 2016

Michelle K. Lee
*Director of the United States Patent and Trademark Office*